(12) United States Patent
Bujard et al.

(10) Patent No.: US 6,933,130 B1
(45) Date of Patent: Aug. 23, 2005

(54) RECOMBINANTS PROCESS FOR PREPARING A COMPLETE MALARIA ANTIGEN, GP190/MSP1

(75) Inventors: Hermann Bujard, Remlerstrasse 9, Heidelberg (DE), D-69120; Ralf Tolle, Ludwigsburg (DE); Weiqing Pan, Heidelberg (DE)

(73) Assignee: Hermann Bujard, Heidelberg (DE)

( * ) Notice: Subject to any disclaimer, the term of this patent is extended or adjusted under 35 U.S.C. 154(b) by 0 days.

(21) Appl. No.: 09/269,874

(22) PCT Filed: Oct. 2, 1997

(86) PCT No.: PCT/EP97/05441

§ 371 (c)(1),
(2), (4) Date: Aug. 2, 1999

(87) PCT Pub. No.: WO98/14583

PCT Pub. Date: Apr. 9, 1998

(30) Foreign Application Priority Data

Oct. 2, 1996 (DE) .......................................... 196 40 817

(51) Int. Cl.[7] ........................... C12P 21/06; C12N 15/09
(52) U.S. Cl. .................... 435/69.1; 435/69.3; 435/71.1; 435/320.1; 435/6; 935/10; 536/23.7
(58) Field of Search ............................... 435/69.1, 69.3, 435/71.1, 320.1, 6, 258.1, 91.4; 536/23.7; 935/10; 530/350

(56) References Cited

FOREIGN PATENT DOCUMENTS

| EP | 0 154 454 A1 | 9/1985 |
| EP | 0 340 359 A1 | 11/1989 |
| EP | 0 359 472 A2 | 3/1990 |
| EP | 0 385 962 A1 | 9/1990 |
| WO | WO 94/28930 | 12/1994 |

OTHER PUBLICATIONS

Blackman et al. (Jul. 1990), "A Single Fragment of a Malaria Merozoite Surface Protein Remains on the Parasite During Red Cell Invasion and is the Target of Invasion–inhibiting Antibodies," *J. Exp. Med.*, vol. 172:379–382.
Chang et al. (Jan. 1996), "A Recombinant Baculovirus 42–Kilodalton C–Terminal Fragment of *Plasmodium falciparum* Merozoite Surface Protein 1 Protects Aotus Monkeys Against Malaria," *Infection and Immunity*, vol. 64(1):253–261.
Etlinger et al. (Oct. 1991), "Ability of Recombinant or Native Proteins to Protect Monkeys Against Heterologous Challenge with *Plasmodium falciparum*," *Infection and Immunity*, vol. 59(10):3498–3503.
Gentz et al. (1988), "Major Surface Antigen p190 of *Plasmodium falciparum*: detection of Common Epitopes Present in a Variety of Plasmodia Isolates," *EMBO Journal*, vol. 7(1):225–230.

Gossen et al. (Jun 1992), "Tight Control of Gene Expression in Mammalian Cells by Tetracycline–Responsive Promoters," *Proc. Natl. Acad. Sci. USA*, vol. 89:5547–5551.
Hall et al. (Sep. 1984), "Major Surface Antigen Gene of a Human Malaria Parasite Cloned and Expressed in Bacteria," *Nature*, vol. 311:379–382.
Heidrich et al. (1989), "The N–Terminal Amino Acid Sequences of the *Plasmodium falciparum* (FCB1) Merozoite Surface Antigens of 42 and 36 Kilodalton, Both Derived from the 185–195–Kilodalton Precursor," *Mol. & Biochem. Parasitology*, vol. 34:147–154.
Herrera et al. (Jan. 1992), "Protection Against Malaria in Aotus Monkeys Immunized with a Recombinant Blood–Stage Antigen Fused to a Unversal T–Cell Epitope: Correlation of Serum Gamma Interferon Levels with Protection," *Infection and Immunity*, vol. 60(1):154–158.
Herrera et al. (May 1990), "Immunization of Aotus Monkeys with Plasmodium falciparum Blood–Stage Recombinant Proteins," *Proc. Natl. Acad. Sci. USA*, vol. 87:4017–4021.
Holder et al. (1988), "Immunization Against *Plasmodium falciparum* with Recombinant Polypeptides Produced in *Escherichia coli*,"*Parasite Immunology*, vol. 10:607–617.
Holder et al. (Sep. 1985), "Primary Structure of the Precursor to the Three Major Surface Antigens of *Plasmodium falciparum* Merozoites," *Nature*, vol. 317:270–273.
Holder et al. (Nov. 1981), "Immunization Against Blood–Stage Rodent Malaria Using Purified Parasite Antigens," *Nature*, vol. 294:361–364.
Majarian et al. (Jun. 1984), "Passive Immunization Against Murine Malaria with an IgG3 Monoclonal Antibody," *J. of Immunology*, vol. 132(6):3131–3137.
Miller et al. (1993), "Analysis of Sequence Diversity in the *Plasmodium falciparum* Merozoite Surface Protein–1 (MSP–1)," *Mol. and Biochem. Parasitology*, vol. 59:1–14.
Myler (1989), "Nucleotide and Deducted Amino Acid Sequence of the gp195 (MSA–1) Gene from *Plasmodium falciparum*," *Nucleic Acids Research*, vol. 17(13):5401.
Pan et al. (1995), "A Direct and Rapid Sequencing Strategy for the *Plasmodium falciparum* Antigen Gene gp190/MSA1," *Mol. and Biochem. Parasitology*, vol. 73:241–244.

(Continued)

Primary Examiner—Patricia A. Duffy
(74) Attorney, Agent, or Firm—Paula A. Borden; Bozicevic, Field & Francis LLP

(57) ABSTRACT

The present invention relates to a method for producing recombinants intended for use in the complete cell-surface protein gp190/MSP1 from plasmodium, especially plasmodium falciparum, as well as the complete DNA sequence of this protein and the appropriate host organisms suited for expressing said sequence, whereby the protein concerned can be entirely synthesized outside the parasite. Also, the inventive method enables sufficient production of above-mentioned protein and its supply as a vaccine. Finally disclosed is a process for stabilizing genes with high At concentration.

28 Claims, 34 Drawing Sheets

OTHER PUBLICATIONS

Figure 1:
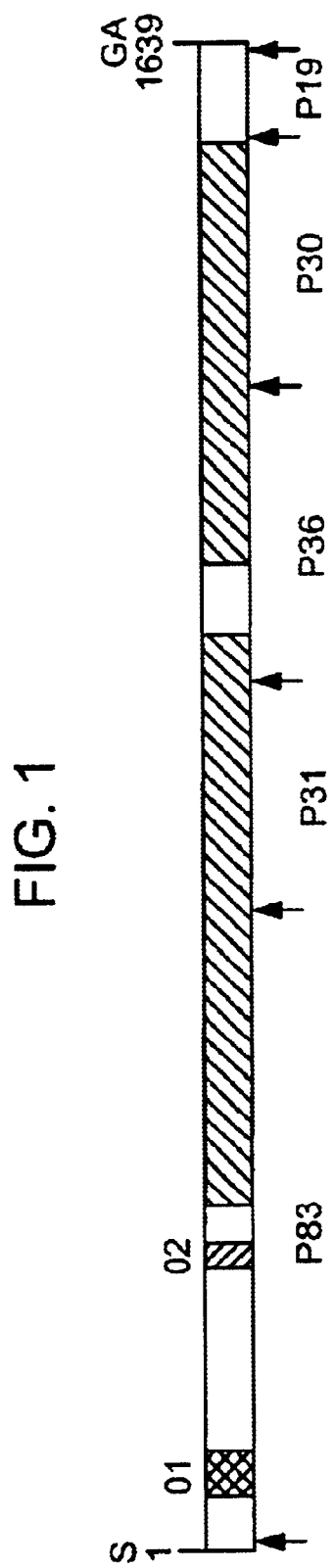

Patarroyo et al. (Aug. 1987), "Induction of Protective Immunity Against Experimental Infection with Malaria Using Synthetic Peptides," *Nature*, vol. 328:629–632.

Perrin et al. (Aug. 1984), "Antimalarial Immunity in Saimiri Monkeys," *J. Exp. Med.*, vol. 160:441–451.

Pfefferkorn et al. (1976), "Toxoplasma gondii: Isolation and Preliminary Characterization of Temperature–Sensitive Mutant," *Experimental Parasitology*, vol. 39:365–376.

Pirson et al. (Mar. 1985), "Characterization with Monoclonal Antibodies of a Surface Antigen of *Plasmodium falciparum* Merozoites," *J. of Immunology*, vol. 134(3):1946–1951.

Siddiqui et al. (May 1987), "Merozoite Surface Coat Precursor Protein Completely Protects Aotus Monkeys Against *Plasmodium falciparum* Malaria," *Proc. Natl. Acad. Sci. USA.*, vol. 84:3014–3018.

Tanabe et al. (1987), "Allelic Dimorphism in a Surface Antigen Gene of the Malaria Parasite *Plasmodium falciparum*," *J. Mol. Biol.*, vol. 195:273–287.

Tolle et al. (Jan. 1993), "A Prospective Study of the Association Between the Human Humoral Immune Response to *Plasmodium falsiparum* Blood Stage Antigen gp190 and Control of Malarial Infections," *Infection and Immunity*, vol. 61(1):40–47.

Kaslow et al., (1994), "Expression and Antigenicity of *Plasmodium falsiparum* Major Merozoite Surface Protein (MSP1$_{19}$) Variants Secreted from Saccharomyces cerevisiae," *Molecular and Biochemical Parasitology*, vol. 63:283–289.

FIG. 3C

DNA sequence of the native (gp190n) and of the synthetic gene (gp190s) for gp190 from FCG-1

```
AS            M   K   I   I   F   F   L   C   S   F   L   F       12
gp190n                                    T T   A               T
gp190s  CGCACGCGTATGAAAAATCATTTTCTTCCTCTGTTCATTTCTGTTT            45
           Mlu I

AS         F   I   I   N   T   Q   C   V   T   H   E   S   Y   Q   E      27
gp190n                     T   A   A   A   T   A   A   T       AGT   A   A
gp190s  TTTATCATCAATACTCAGTGCGTGACCCACGAATCCTATCAGGAG                      90

AS         L   V   K   K   L   E   A   L   E   D   A   V   L   T   G      42
gp190n         T   C   A   A           A               A   ATG   A   T
gp190s  CTGGTTAAGAAACTGGAAGCTTTGGAAGATGCCGTCCTTACCGGA                     135

AS         Y   S   L   F   Q   K   E   K   M   V   L   N   E   G   T      57
gp190n         T   TT  A   T   A   A   A   A       AT  A       A   A
gp190s  TACAGCCTGTTCCAGAAGGAGAAGATGGTGCTGAATGAAGGGACG                     180
```

FIG. 3D

```
AS     S G T A V T T S T P G S S K G S                    72
gp190n         A A T     T T   T   A G T A
gp190s AGTGGCACGGCCGTTACAACCAGCACACCCGGTTCTAAAGGGTCT      225

AS     V A S G G G S V A S G G S                         87
gp190n   T   TCA   T A C A T T A T C A
gp190s GTGGCTAGCGGTGGCTCCGGTGTCTGTGGCCTCTGGGGGTTCC        270

AS     V A S G G S V A S G G S V A S                    102
gp190n       T T A T TCA T T       T   TTCA
gp190s GTCGCCTCCGGCGGGTCCAGCAGCGTGGCTCAGTGGCTCAAGC        315

AS     G G S G N S R R T N P S D N S                    117
gp190n       T     A T   TTCAA C T A     T A T T A
gp190s GGCGGGTTCCGGGAACAGTCGAAGAACCAATCCATCTGACAACTCT     360

AS     S D S D A K S Y A D L K H R V                    132
gp190n       T   A T T A T   T TT A A A   A
gp190s AGCGATTCCGACGCCAAGTCCTACGCCGACCTCAAGCACCGAGTG      405

AS     R N Y L L T I K E L K Y P Q L                    147
gp190n   C   T CT GT A     A A C A T T AC C
gp190s AGAAACTATCTCCTCACTATCAAGGAGCTGAAGTACCCCACAGTTG     450
```

FIG. 3E

```
AS        F  D  L  T  N  H  M  L  T  L  C  D  N  I  H        162
gp190n       T TT A                       T A TT    T
gp190s    TTCGACCTCACTAATCATATGCTGACACTGTGATAACATTCAT        495

AS        G  F  K  Y  L  I  D  G  Y  E  E  I  N  E  L        177
gp190n       T                  TA  T A T      T  A
gp190s    GGCTTCAAATATCTGATTGACGGTTACGAAGAGATCAATGAACTC        540

AS        L  Y  K  L  N  F  Y  F  D  L  L  R  A  K  L        192
gp190n    T A    T  A  A  C  T  T  T  T  AT  A  A  T A
gp190s    CTGTACAAGTTGAATTTCTACTTCGACTTGCTAAGGGCCAAACTG        585

AS        N  D  V  C  A  N  D  Y  C  Q  I  P  F  N  L        207
gp190n              T  A  T  T           A  T     C T
gp190s    AATGACGTTTGCGCCAATGACTATTGTCAAATTCCATTCAATTTG        630

AS        K  I  R  A  N  E  L  D  V  L  K  K  L  V  F        222
gp190n       A  TC T  A  T  A  A     C  T  A   AC T  G
gp190s    AAGATCAGAGCCAACGAGTTGGACGTATTGAAGAAGTTGGTCTTC        675
```

FIG. 3F

```
AS        G  Y  R  K  P  L  D  N  I  K  D  N  V  G  K              237
gp190n       A  A     A  AT  A     T  T  A  T     A     A
gp190s    GGATATCGCAAGCCTCTCGACAACATCAAGGACAATGTGGAAAG              720

AS        M  E  D  Y  I  K  K  N  K  K  T  I  E  N  I              252
gp190n                   C     A     A  A     A  A  T  A
gp190s    ATGGAAGATTATATTAAAAAGAATAAGAAGACCATCGAGAACATT             765

AS        N  E  L  I  E  E  S  K  K  K  T  I  D  K  N  K           267
gp190n       T  AT  A  T        AGT  G  A  A  T  T
gp190s    AACGAGCTGATCGAAGAATCCAAAAAGACCATAGACAAAAATAAG             810

AS        N  A  T  K  E  E  E  K  K  K  L  Y  Q  A  Q              282
gp190n             T  A  A        A  A  A  A     A  T  A
gp190s    AATGCAACCAAGGAGGAAGAAAAAGAAGTTGTACCAGGCCCAG               855

AS        Y  D  L  S  I  Y  N  K  Q  L  E  E  A  H  N              297
gp190n       T     T  T  T  C  T        AT  A        A        T
gp190s    TACGACCTGTCCATCTATAACAAACAGCTTGAAGAAGCCCATAAC             900
```

FIG. 3G

```
AS      L  I  S  V  L  E  K  R  I  D  T  L  K  K  N                  312
gp190n        T  A     A        T T  A     A  T T  A  A     A
gp190s  CTCATCAGCGTACTGGAGAAGCGCATAGACACCCTCAAGAAGAAT                 945

AS      E  N  I  K  E  L  L  D  K  I  N  E  I  K  N                  327
gp190n        C  T  G     T  A  T T  A                    A
gp190s  GAAAATATCAAAGAACTGCTCGACAAGATTAATGAAATTAAGAAT                 990

AS      P  P  P  A  N  S  G  N  T  P  N  T  L  L  D                  342
gp190n     C  A  G        T     A  T  A  A  T  C T  T
gp190s  CCTCCGCCAGCCAACTCTGGGAACACCCCTAACACGCTGCTGGAC                 1035

AS      K  N  K  K  I  E  E  H  E  K  E  I  K  E  I                  357
gp190n              A  A  C     A     A     A  A  A  T
gp190s  AAGAACAAGAAGATAGAGGAGCACGAGAAAGAGATCAAAGAGATC                 1080

AS      A  K  T  I  K  F  N  I  D  S  L  F  T  D  P                  372
gp190n           T        A  T  T  T    A G  T  A       A
gp190s  GCCAAAACCATTAAGTTCAACATAGATTCTCTCTTTACTGATCCC                 1125
```

FIG. 3H

```
AS      L E L E Y Y L R E K N K N I D              387
gp190n          AT A A   T A  A A A  T T
gp190s  CTTGAGCTGGAGTACTACTTGAGAGAGAAGAATAAGAATATAGAC  1170

AS      I S A K V E T K E S T E P N E              402
gp190n  AAGT  A G T A
gp190s  ATCTCCGCCAAAGTCGAGACAAAGGAATCAACCGAACCTAATGAA  1215

AS      Y P N G V T Y P L S Y N D I N              417
gp190n         A   A T T T T A         T
gp190s  TATCCCAATGGTGTGACGTACCCTCTGTCTTATAACGATATCAAC  1260

AS      N A L N E L N S F G D L I N P              432
gp190n         T       T  TCT  T  T A  T A
gp190s  AACGCTCTCAACGAGCTCAATAGCTTCGGTGACTTGATTAACCCC  1305

AS      F D Y T K E P S K N I Y T D N              447
gp190n    T                A   A C A  T T
gp190s  TTCGATTATACGAAAGAACCCTCTAAGAATATCTACACAGACAAT  1350
```

FIG. 3I

```
AS       E  R  R  K  K  F  I  N  E  I  K  E  K  I  K  I          462
gp190n      A     A  A  C  A  T     T     A  A  T     A
gp190s   GAGAGAAGAAGTTATCAACGAAATCAAGGAGAAGATCAAAATT              1395

AS       E  K  K  K  I  E  S  D  K  K  S  Y  E  D  R             477
gp190n      A  A  A           ATC  T  A     TC        A  A
gp190s   GAGAAGAAGAAAATTGAGAGTGACAAGAAAAGTTACGAAGACCGC            1440

AS       S  K  S  L  N  D  I  T  K  E  Y  E  K  L  L             492
gp190n   TCT   GTC  T     T        A  A  A     A     AT  A  T
gp190s   AGCAAAAGTCTAAACGATATCACTAAAGAGTATGAAAAGCTGCTG            1485

AS       N  E  I  Y  D  S  K  F  N  N  N  I  D  L  T             507
gp190n         T        AG              T     T  A  TT  A  T
gp190s   AACGAGATCTATGATTCCAAATTCAACAATAACATCGACCTGACC            1530

AS       N  F  E  K  M  M  G  K  R  Y  S  Y  K  V  E             522
gp190n      T     A              T     A  A  T  A  T
gp190s   AACTTCGAGAAAATGATGGGAAAACGGTACTCTTACAAAGTGGAG            1575
```

FIG. 3J

```
AS          K  L  T  H  H  N  T  F  A  S  Y  E  N  S  K      537
gp190n                                                  A
gp190s      T
         AAACTGACACACCATAATACCTTTGCATCCTATGAGAATTCTAAG        1620

AS          H  N  L  E  K  L  T  K  A  L  K  Y  M  E  D      552
gp190n               A  T  A  A        A        A  T
gp190s
         CATAATCTTGAGAAGCTCACCAAAGCTCTTAAGTATATGGAGGAC        1665

AS          Y  S  L  R  N  I  V  V  E  K  E  L  K  Y  Y      567
gp190n      T  AA     T  A  A  T  A        T  A        T
gp190s
         TATTCTCTGCGGAACATTGTTGTGGAGAAGAACTAAAGTATTAC         1710

AS          K  N  L  I  S  K  I  E  N  E  I  E  T  L  V      582
gp190n         A  T  A        C  A  A        T     T  A  AT A
gp190s
         AAGAATCTCATAAGTAAGATCGAAAACGAGATCGAGACGCTTGTT        1755

AS          E  N  I  K  K  D  E  E  Q  L  F  E  K  K  I      597
gp190n         A  T     A  A                 C  T     A  A  A
gp190s
         GAGAACATTAAGAAGGATGAAGAACAGTTGTTTGAGAAGAAGATT        1800
```

FIG. 3K

```
AS       T  K  D  E  N  K  P  D  E  K  I  L  E  V  S                    612
gp190n                T
gp190s                                    A  A  TT A  A  A  T
         ACAAAGACGAAAATAAACCAGATGAGAAGATCCTGGAGTCTCC                     1845

AS       D  I  V  K  V  Q  V  Q  K  V  L  L  M  N  K                    627
gp190n            C        A        A        T  A              A
gp190s                                 A  A  TT A  TA
         GATATTGTTAAAGTCCAAGTGCAGAAGGTGCTCCTCATGAACAAG                   1890

AS       I  D  E  L  K  K  T  Q  L  I  L  K  N  V  E                    642
gp190n            C              T  A        A
gp190s                                    TG T  A  A  T  A  A
         ATTGATGAACTCAAGAAGACTCAACTCATTCTGAAGAACGTGGAG                   1935

AS       L  K  H  N  I  H  V  P  N  S  Y  K  Q  E  N                    657
gp190n                         T  C     TC T  C  A  A  A     A
gp190s
         TTAAAACATAATATACATGTGCCGAATAGTTATAAGCAGGAGAAT                   1980

AS       K  Q  E  P  Y  Y  L  I  V  L  K  K  E  I  D                    672
gp190n            A        T  TT T  TA T  GT G  A     A  T     T
gp190s
         AAGCAGGAACCATACTACCTCATCGTACTCAAGAAAGAGATAGAC                   2025
```

FIG. 3L

```
AS         K  L  K  V  F  M  P  K  V  E  S  L  I  N  E              687
gp190n                                         T  A                      
gp190s  AAACTGAAAGTGTTCATGCCCAAAGTCGAGAGCCTGATCAACGAA                 2070
                                               T  G  A  ATCAT  AT

AS         E  K  K  N  I  K  T  E  G  Q  S  D  N  S  E              702
gp190n     A  A  A  A           A                                        
gp190s  GAGAAGAAGAACATTAAAACTGAAGGACAGTCAGATAACTCCGAG                 2115
                                T  A  G        T  G  A

AS         P  S  T  E  G  E  I  T  G  Q  A  T  T  K  P              717
gp190n     A  A  C           A     A  A  A  T  A  A  T                  
gp190s  CCTTCCACAGAAGGAGAGATAACCGGACAGGCTACCACCAAGCCC                 2160

AS         G  Q  Q  A  G  S  A  L  E  G  D  S  V  Q  A              732
gp190n                    A  A  A  T  A           A     A                
gp190s  GGACAACAGGCCGGTTCAGCTCTCGAAGGCGATAGCGTGCAAGCT                 2205
                                         TCA  A     A

AS         Q  A  Q  E  Q  K  Q  A  Q  P  P  V  P  V  P              747
gp190n     A  A  A  A  A  A  A  A  A     A  A  A                        
gp190s  CAAGCCACAAGAGCAGAAGCAGGCACAGCCTCCAGTGCCAGTGCCC                 2250
```

FIG. 3M

```
AS       V  P  E  A  K  A  Q  V  P  T  P  P  A  P  V        762
gp190n      A     A     A     A  C  A           A  A  A
gp190s   GTTCCAGAGGCTAAAGCTCAAGTGCCTACACCACCAGCTCCTGTG        2295

AS       N  N  K  T  E  N  V  S  K  L  D  Y  L  E  K        777
gp190n      T  A  T  A     TTC     T  A  T  T  A  A
gp190s   AATAACAAGACCGAGAATGTCAGCAAACTGGACTACCTTGAGAAG        2340

AS       L  Y  E  F  L  N  T  S  Y  I  C  H  K  Y  I        792
gp190n   T  A     A  TT  A        T  A  T  A  T        T
gp190s   CTCTATGAGTTCCTGAATACATCCTACATCTGCCACAAATATATC       2385

AS       L  V  S  H  S  T  M  N  E  K  I  L  K  Q  Y        807
gp190n   T  G     T  A     TCA           A     AT A     A T
gp190s   CTCGTCTCTCACAGCACTATGAACGAGAAGATTCTTAAACAGTAC       2430

AS       K  I  T  K  E  E  E  S  K  L  S  C  D  P           822
gp190n      A  T  A     G  A  A  C     T  AAGT A
gp190s   AAGATAACCAAGGAAGAGGAGAGTAAACTGTCCTCTTGTGATCCA       2475
```

FIG. 3N

```
AS       L  D  L  L  F  N  I  Q  N  N  I  P  V  M  Y                    837
gp190n         T  A  T     T     A  A  T     A  T  A
gp190s   CTGGACCTGCTGTTCAATATCCAGAACAACATTCCCGTTATGTAT                   2520

AS       S  M  F  D  S  L  N  N  S  L  S  Q  L  F  M                    852
gp190n                           T        A  A  T  A        T
gp190s   TCTATGTTCGATAGCCTCAACAATTCTCTCAACTGTTCATG                       2565

AS       E  I  Y  E  K  E  M  V  C  N  L  Y  K  L  K                    867
gp190n      A  T     A  A  A     T  T     TT  A        T  G
gp190s   GAGATATATGAGAAGGAGATGGTCTGCAACCTGTATAAACTCAAA                   2610

AS       D  N  D  K  I  K  N  L  L  E  E  A  K  K  V                    882
gp190n      T  T     A     A     TT AT A        G  A  A  A
gp190s   GACAACGACAAGATTAAGAACCTTCTGGAGGAAGCTAAGAAGGTC                   2655

AS       S  T  S  V  K  T  L  S  S  S  S  M  Q  P  L                    897
gp190n            A     A        T  AAGTTCA  A           T  A
gp190s   TCCACCTCTGTTAAAACTCTCTCCAGTCCATGCAACCACTG                       2700
```

FIG. 30

```
AS      S  L  T  P  Q  D  K  P  E  V  S  A  N  D  D  D       912
gp190n                AT  A              G  T  A     A  T  A  T  T     T
gp190s  TCTCTCACACCTCAAGACAAGCCCGAAGTGAGCGCTAACGACGAC         2745

AS      T  S  H  S  T  N  L  N  N  S  L  K  L  F  E          927
gp190n     A  A  T  A     T  T  G     TAGTT  A     T  A        A
gp190s  ACCTCTCACTCGACCAACCTTAATAACTCACTGAAACTGTTTGAG         2790

AS      N  I  L  S  L  G  K  N  K  N  I  Y  Q  E  L          942
gp190n          AT  AG     T  A  A  C  A  T  A           T  A
gp190s  AACATCCTGTCTCTCGGCAAGAATAAGAACATCTACCAAGAACTT         2835

AS      I  G  Q  K  S  S  E  N  F  Y  E  K  I  L  K          957
gp190n           A  T  A     AGTAGT  A        T  T  A           T  A
gp190s  ATTGGACAGAAATCGTCCGAGAACTTCTACGAGAAGATACTGAAA         2880

AS      D  S  D  T  F  Y  N  E  S  F  T  N  F  V  K          972
gp190n        T        T           T     T  ATCT  T  A  T  T  A
gp190s  GACAGCGACACATTCTATAACGAGAGCTTCACTAACTTCGTGAAA         2925
```

FIG. 3P

```
AS     S K A D D I N S L N D E S K R                              987
gp190n           T       T AT G T       A  A G
gp190s TCTAAAGCCGATGATATCAACTCTCTTAACGATGAATCTAAACGT              2970

AS     K K L E E D I N K L K K T L Q                              1002
gp190n       AT A    A T T       AT A A A  TT A  G
gp190s AAGAAGCTGGAAGAACATCAATAAGCTGAAGAAGACACTGCAA                 3015

AS     L S F D L Y N K Y K L K L E R                              1017
gp190n T ATCA T   TT A T T AT T TA T  TA  A
gp190s CTGAGCTTCGACCTGTACAACAAGTACAAACTGAAACTGGAGAGA               3060

AS     L F D K K K T V G K Y K M Q I                              1032
gp190n TA  T T A    A  T T A     A   AT
gp190s CTCTTCGACAAGAAGAAGACAGTCGGCAAGTATAAGATGCAGATC               3105

AS     K K L T L L K E Q L E S K L N                              1047
gp190n       A  A AC T    T AT A A A AT A  TCA  T G T
gp190s AAGAAGTTGACTCTGCTCAAGGAGCAGCTTGAAAGCAAACTCAAC                3150
```

FIG. 3Q

```
AS       S  L  N  N  P  K  H  V  L  Q  N  F  S  V  F                      1062
gp190n               T                T  C  A  G  T  TAA    T  T  T
gp190s   TCACTGAACAATCCGAAACACGTACTGCAGAACTTCTCAGTGTTC                     3195

AS       F  N  K  K  K  E  A  E  I  A  E  T  E  N  T                      1077
gp190n      T        A  A  A     T  A  A  A  A  T  A        A
gp190s   TTCAACAAGAAGAAGCCGAGATCGCCGAGACAGAGAACACT                         3240

AS       L  E  N  T  K  I  L  L  K  H  Y  K  G  L  V                      1092
gp190n   TAA     A     A  AT  AT  G        T  T     A  T  T
gp190s   CTGGAGAACACCAAGATTCTTCTCAAACACTACAAAGGCCTCGTC                     3285

AS       K  Y  Y  N  G  E  S  S  P  L  K  T  L  S  E                      1107
gp190n             A              TAA          AT  A  A     T  AAGT   A
gp190s   AAGTATTATAATGGCGAGTCTTCCCTGAAGACTCTCTCCGAG                        3330

AS       E  S  I  Q  T  E  D  N  Y  A  S  L  E  N  F                      1122
gp190n   ATCA    T  AAA              A        T  T     TT  AA        T
gp190s   GAGAGCATCCAGACCGAGGATAACTACGCCAGCCTCGAGAACTTC                     3375
```

FIG. 3R

```
AS       K  V  L  S  K  L  E  G  K  L  K  D  N  L  N                1137
gp190n      A  AT AAG    AT A     A  AT A     T TT A  T
gp190s   AAGGTCCTGTCTAAGCTCGAAGGCAAGCTGAAGGACAACCTGAAC                3420

AS       L  E  K  K  K  L  S  Y  L  S  S  G  L  H  H                1152
gp190n   T  A        A     AT ATCA TA AT       TA    T
gp190s   CTGGAGAAGAAGAAGCTCAGTCAGCTACCTCTCTAGCGGACTGCATCAC            3465

AS       L  I  A  E  L  K  E  V  I  K  N  K  N  Y  T                1167
gp190n   TA T  T     AT A     A     A  A  T  A  T T A
gp190s   CTGATCGCCGAGCTCAAGGAAGTCATTAAGAACAAGAACTACACC                3510

AS       G  N  S  P  S  E  N  N  T  D  V  N  N  A  L                1182
gp190n      T     TCT       T     A     GT TC T  T A
gp190s   GGCAATAGCCCAAGCGAGAATAATACAGACGTGAATAACGCCACTG               3555

AS       E  S  Y  K  K  F  L  P  E  G  T  D  V  A  T                1197
gp190n                  A  AT C A              T  A  A
gp190s   GAATCTTACAAGAAGTTCCTGCCTGAAGGAACAGATGTCGCCACT                3600
```

FIG. 3S

```
AS       V  V  S  E  S  G  S  D  T  L  E  Q  S  Q  P                  1212
gp190n         T        AG  A            TA  A  AAG        A
gp190s   GTGGTGTCTGAATCTGGCTCCGACACTGGAGCAGTCTCAACCT                   3645

AS       K  K  P  A  S  T  H  V  G  A  E  S  N  T  I                  1227
gp190n         A  A     A              A  A     TC     A
gp190s   AAGAAGCCTGCATCTACTCATGTCGGAGCCGAGTCCAATACAATT                 3690

AS       T  T  S  Q  N  V  D  D  E  V  D  D  V  I  I                  1242
gp190n      A        AA  T        A  A  A           A    A
gp190s   ACCACACATCTCAGAACGTCGACGATGAGGTCGATGACGTCATCATT               3735

AS       V  P  I  F  G  E  S  E  E  D  Y  D  D  L  G                  1257
gp190n         A     A  T  A ATC   A  A  T     TT  A     A
gp190s   GTGCCTATCTTCGGCGAGAGCGAGGAGGACTACGATGACCTCGGC                 3780

AS       Q  V  V  T  G  E  A  A  A  A  A  S  V  I  D  N               1272
gp190n      A  A  A  A  A  A  A  A  A        A
gp190s   CAGGTGGTCACCGGTGAGGCTGTCACTCCTTCCGTGATTGATAAC                  3825
```

```
AS       D  P  Y  K  F  L  N  K  E  K  R  D  K  F  L           1362
gp190n      T     T  A  T  T     A  A  A        CT A
gp190s   GACCCATACAAGTTCCTCAATAAAGAGAAGAGGGATAAATTTCTG          4095

AS       S  S  Y  N  Y  I  K  D  S  I  D  T  D  I  N           1377
gp190n   AGC   T     T  T     T  A  A  T  G     A
gp190s   TCTAGTTACAACTATATCAAGGACTCCATCGACACCGATATCAAT          4140

AS       F  A  N  D  V  L  G  Y  Y  K  I  L  S  E  K           1392
gp190n      T  A              T  T  A     T  A  AT ATC
gp190s   TTCGCTAATGATGTGCTGGGGTATTACAAGATCCTGAGCGAAAAA          4185

AS       Y  K  S  D  L  D  S  I  K  K  Y  I  N  D  K           1407
gp190n      T     A     TT A  T  A        A           C  A
gp190s   TACAAGTCTGACCTTGACTCTATTAAAAAGTATATCAACGATAAG          4230

AS       Q  G  E  N  E  K  Y  L  P  F  L  N  N  I  E           1422
gp190n      T  A        G  C  T     TT A  C  T  T  G
gp190s   CAAGGCGAGAATGAAAAATATCTGCCCTTCCTGAATAACATCGAA          4275
```

FIG. 3V

```
AS     T  L  Y  K  T  V  N  D  K  I  D  L  F  V  I          1437
gp190n    T  A  T  A     T  T  T     T  T  A  T
gp190s ACCCTGTACAAGACAGTGAACGACAAATGACCTCTTCGTAATT           4320

AS     H  L  E  A  K  V  L  N  Y  T  Y  E  K  S  N          1452
gp190n    T  A  A  A  A  T  A  T     A  T        ATCA  C
gp190s CACCCTGGAGGCCAAGGTCCTCAACTATACTTACGAGAAGAGCAAT         4365

AS     V  E  V  K  I  K  E  L  N  Y  L  K  T  I  Q          1467
gp190n    A           A     A  A  T  T  T  A        T
gp190s GTGGAAGTTAAAATCAAGGAGCTGAACTACCTCAAAACAATCCAA          4410

AS     D  K  L  A  D  F  K  K  N  N  N  F  V  G  I          1482
gp190n             AT                                 T
gp190s GACAAGCTGGCAGATTTCAAGAAAAATAACAATTTCGTCGGAATT          4455

AS     A  D  L  S  T  D  Y  N  H  N  N  L  L  T  K          1497
gp190n    T     TT  A  A  A        T  T  CT  AT     A
gp190s GCAGACCTGTCTACCGATTATAACCACAACAATCTCCTGACCAAG          4500
```

FIG. 3W

```
AS        F L S T G M V F E N L A K T V           1512
gp190n      C TAGT A T   T T   T T C T
gp190s    TTTCTGTCCACTGGCATGGTTCGAAAACCTGCCAAAACAGTG  4545

AS        L S N L L D G N L Q G M L N I           1527
gp190n    T ATCT     TA T  A T  A T A
gp190s    CTGAGCAATCTGCTCGACGGCAACCTGCAGGGCATGCTGAACATC  4590

AS        S Q H Q C V K K Q C P Q N S G           1542
gp190n      A A        A  A  A T A A TCT A
gp190s    TCCCAGCACCAATGCGTGAAGAAACAGTGCCCCAGAATAGCGGC  4635

AS        C F R H L D E R E E C K C L L           1557
gp190n                        A T A T A  A T A T A
gp190s    TGTTTCAGGCATCTGGACGAGAGGGAAGAGTGCAAGTGTCTCCTG  4680

AS        N Y K Q E G G D K C V E N P N P         1572
gp190n      T                 T  A T T A T  T
gp190s    AACTACAAACAAGAAGGAGATAAGTGCGTGGAGAACCCAAACCCT  4725
```

FIG. 3X

```
AS       T C N E N N G G C D A D A K C          1587
gp190n   T   T   C   T     T A   T A   C   T
gp190s   ACCTGCAATGAAAACAATGGCGGTGTGACGCCGATGCTAAATGC  4770

AS       T E E D S G S N G K K I T C E          1602
gp190n       A       TTCA TAGC              T   A
gp190s   ACCGAGGAAGACAGCGGCTCTAACGGAAAGAAAATCACATGCGAG  4815

AS       C T K P D S Y P L F D G I F C          1617
gp190n             A   T T T         T   T T   C
gp190s   TGTACTAAGCCCGACTCCTATCCACTCTTCGACGGGATTTTTTGC  4860

AS       S S S N F L G I F F L L I L M          1632
gp190n   AGTTC       C   T A A   A CA   T AT A   A
gp190s   TCCAGCTCTAATTTCCTGGGCATTCTTCTTCTGCTGATCCTCATG  4905

AS       L I L Y S F I *      *              1639
gp190n   T A   AT A         T        T
gp190s   CTGATCCTGTACAGCTTCATCTAATAGATCGATGG  4940
                                stop codon  Cla I
```

FIG. 3Y gp190s1 Sequence

N'-terminus

```
DNA Sequence    GC ACGCGTATGAAAATC ——————  AGCTCTAATTAATAGGCGGCCGCATCGATGC
AA Sequence        MluI Met Lys Ile            Ser Ser Asn  stop codon  NotI    ClaI
AA Position             1   2   3              1619 1620 1621
```

C'-terminus gp190s2 Sequence

```
DNA Sequence    GC GGATCCGTGACCCAC ——————  AGCTCTAATTAATAGGCGGCCGCATCGATGC
AA Sequence        BamHI Val Thr His           Ser Ser Asn  stop codon  NotI    ClaI
AA Position              20  21  22            1619 1620 1621
```

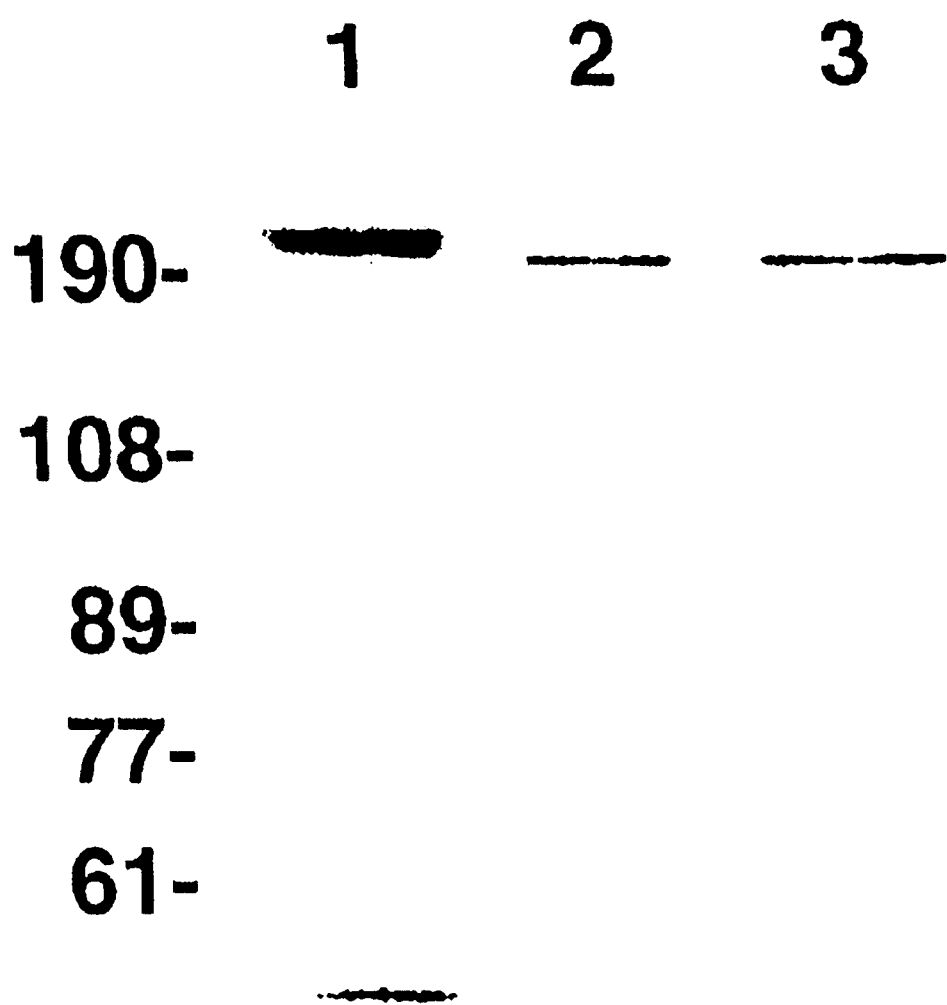

RECOMBINANTS PROCESS FOR PREPARING A COMPLETE MALARIA ANTIGEN, GP190/MSP1

This application is a 35 U.S.C. §371 filing of International Patent Application No. PCT/EP97/05441, filed Oct. 2, 1997. This application claims priority benefit of German Patent Application. No. DE 19640817.2, filed Oct. 2, 1996.

The invention concerns a recombinant manufacturing process for the complete malaria antigen gp190/MSP1, as well as separate naturally-occurring domains and parts of the same, by expression of a synthetic DNA sequence. The invention concerns in addition the DNA sequences produced by the process and the host organisms used for the expression of the DNA sequences. In addition the invention concerns the use of the complete malaria antigen as well as parts thereof as a vaccine for immunization against malaria.

Finally the invention under consideration concerns a stabilization process for AT-rich genes, as well as stabilized genes which are characterized by a reduced AT content.

Malaria is one of the most significant infectious diseases in the world. According to WHO reports, in 1990 40% of the world population in 99 countries was exposed to the risk of malaria. At the same time its distribution is enormously on the increase. This may be ascribed above all to intensive development of resistance in the parasites causing malaria, promoted by the recommendation and use as prophylactics of the drugs intended for treatment. Besides the search for new and effective chemotherapeutic agents hope is nowadays directed towards the development of vaccines, since people in areas of the world where malaria is epidemic do manage to develop some kinds of immunity. As well as a natural resistance to malaria, such as that found in heterozygous carriers of the sickle-cell gene and people with thalassaemia and glucose-6-phosphate dehydrogenase deficiency, in the course of malarial infection in humans immune mechanisms can be stimulated which express themselves in a heightened capacity for resistance to the Plasmodia. Consequently the course of the disease in populations exposed to severe epidemics is generally less threatening than in persons exposed to the infection less frequently or for the first time.

The main problem in the development of a vaccine is the identification of an antigen which can induce protective immunity, since there is no easily accessible well-defined animal model available for the four parasites affecting man. The organism causing malaria belongs to the *Plasmodium* group, of which infection with one of the four parasites *Plasmodium vivax, Plasmodium ovale, Plasmodium malariae* or *Plasmodium falciparum* results from the bite of *Anopheles* mosquitoes. Of these parasites *Plasmodium falciparum* is the most dangerous and the most widely distributed.

The main surface protein of the merozoite, the invasive form of the blood stage of the malaria parasite *Plasmodium falciparum* and other malaria parasites such as *P. vivax*, is a 190–220 kD glycoprotein. Late in the development of the parasite this precursor is processed into smaller proteins, which can however be isolated from merozoites as a unitary complex. By means of a glycosylphosphatidyl-inositol bond this complex is coupled to the merozoite membrane. The sequences of the gp190 proteins of various *P. falciparum* strains fall into two groups, between which intragenic recombination is frequent. In general the protein consists of many highly conserved regions, of a dimorphic zone to which in each case one of two alleles belongs, and of two relatively small oligomorphic blocs in the N-terminal zone (Tanabe, K., Mackay, M., Goman, M. and Scaife, J. G. (1987), Allelic dimorphism in a surface antigen gene of the malaria parasite *Plasmodium falciparum*. J. Mol. Biol. 195, 273–287, Miller, L. H., Roberts, T., Shahabuddin, M. and McCutchan, T. F. (1993), Analysis of sequence diversity in the *Plasmodium falciparum* merozoite surface protein-1 (MSP-1). Mol. Biochem. Parasitol. 59, 1–14).

Already early on gp190/MSP1 was considered as a possible candidate for a vaccine. In the rodent model active protection against infection with rodent parasites was obtained following immunization with the analogous protein. Passive protection could be procured with antibodies directed against this protein (see also Holder, A. A. and Freeman, R. R. (1981), Immunization against blood-stage rodent malaria using purified parasite antigens, Nature 294, 361–364; Marjarian, W. R., Daly, T. M., Weidanz, W. P. and Long, C. A. (1984), Passive immunization against murine malaria with an IgG3 monoclonal antibody, J. Immunol. 132, 3131–3137). The data which ought to support this assumption are nevertheless in details not statistically significant.

There are in addition, a number of monoclonal antibodies which in vitro inhibit the invasion of erythrocytes by *P. falciparum* and are directed against gp190/MSP1 (Pirson, P. J. and Perkins, M. E. (1985), Characterization with monoclonal antibodies of a surface antigen of *Plasmodium falciparum* merozoites. J. Immunol. 134, 1946–1951; Blackman, M. J., Heidrich, H., Donachie, S., McBride, J. S. and Holder, A. A. (1990), A single fragment of a malaria merozoite surface protein remains on the parasite during red-cell invasion and is the target of invasion-inhibiting antibodies. J. Exp. Med. 172, 379–382).

Finally, a series of vaccine studies have been carried out with gp190/MSP1 from *P. falciparum* on primates, particularly on *Aotus* and *Saimiri* monkeys (see also Perrin, L. H., Merkli, B., Loche, M., Chizzolini, C., Smart, J. and Richle, R. (1984), Antimalarial immunity in Saimiri monkeys. Immunization with surface components of asexual blood stages, J. Exp. Med. 160, 441–451; Hall, R., Hyde, J. E., Goman, M., Simmons, D. L., Hope, I. A., Mackay, M. and Scaife, J. G. (1984), Major surface antigen gene of a human malaria parasite cloned and expressed in bacteria, Nature 311, 379–382; Siddiqui, W. A., Tam, L. Q., Kramer, K. J., Hui, G. S. N., Case, S. E., Yamaga, K. M., Chang, S. P., Chan, E. B. T. and Kan, S.-C. (1987), Merozoite surface coat precursor protein completely protects *Aotus* monkeys against *Plasmodium falciparum* malaria, Proc. Natl. Acad. Sci. USA 84, 3014–3018; Ettlinger, H. M., Caspers, P., Materile, H., Schoenfeld H.-J., Stueber, D. and Takacs, B. (1991), Ability of recombinant or native proteins to protect monkeys against heterologous challenge with *Plasmodium falciparum*, Inf. 1 mm. 59, 3498–3503; Holder, A. A., Freeman, R. R. and Nicholls, S. C. (1988), Immunization against *Plasmodium falciparum* with recombinant polypeptides produced in *Escherichia coli*, Parasite Immunol. 10, 607–617; Herrera, S., Herrera, M. A., Perlaza, B. L., Burki, Y., Caspers, P., Doebeli, H., Rotmann D. and Certa, U. (1990), Immunization of *Aotus* monkeys with *Plasmodium falciparum* blood-stage recombinant proteins, Proc. Natl, Acad. Sci. USA 87, 4017–4021; Herrera, M. A., Rosero, F., Herrera, S., Caspers, P., Rotmann, D., Sinigaglia, F. and Certa, U. (1992), Protection against malaria in *Aotus* monkeys immunized with a recombinant blood-stage antigen fused to a universal T-cell epitope; correlation of serum gamma interferon levels with protection, Inf. Imm. 60, 154–158; Patarroyo, M. E., Romero, P., Torres, M. L., Clavijo, P., Moreno, A., Martinez A., Rodriquez, R., Guzmann, F. and Cabezas, E. (1987), Induction of protective immunity against experimental infection with malaria using synthetic peptides, Nature 328, 629–632). In these vaccine studies two premises may be distinguished:

Use of material isolated from parasites, and

Administration of material procured in heterologous systems of expression.

The latter consists as a rule of relatively small segments of the total protein. Although the results of the inoculations carried out preliminarily on monkeys indicate that gp190/MSP1 could bring about protection, all the experiments carried out on primates have two problems, which place such a conclusion in question:

(a) they were carried out on too small groups of animals (b) they were not repeated.

The results and the conclusions drawn from them are consequently not statistically confirmed. Besides/the difficulty of access to suitable monkeys there remains the main basic problem, that it has so far not been possible to manufacture good vaccination material in a suitable quantity.

On the other hand, after the sequencing of the gp190 gene from the K1 and MAD20 strains of *Plasmodium falciparum* overlapping fragments could be expressed in *E. coli*. With this material epidemiological studies in West Africa showed that in the adolescent group a correlation existed between antibody titre against gp190/MSP1 fragments on one hand and protection from parasite infection on the other. In addition the titre also appeared to correlate with the capacity to control the parasitaemia even at a low level (Tolle et al. (1993): A prospective study of the association between the human humoral immune response to *Plasmodium falciparum* blood stage antigen gp190 and control of malarial infections, Infect Immun. 61, 40–47). These results are supplemented by new investigations on *Aotus* monkeys in the framework of the present invention. Here an enhanced protection against infection with the parasite was attained because protein preparations from *Plasmodium falciparum*, which consisted predominantly of unprocessed gp190/MSP1, had been used as vaccine. The monkeys with the highest antibody titres against gp190/MSP1 were the best protected. These results eventually indicated gp190 as a most promising candidate for a vaccine against tropical malaria.

By some groups of workers the C-terminal domain of gp190 (p19 or p42) is assigned a particular role in the immunity mediated by gp190 (see also Chang, S. P., Case, S. E., Gosnell, W. L., Hashimoto, A., Kramer, K. J., Tam, L. Q., Hashiro, C. Q., Nikaido, C. M., Gibson, H. L., Lee-Ng, C. T., Barr, P. J., Yokota, B. T. and Hui, G. S. N. (1996), A recombinant baculovirus 42-kilodalton C-terminal fragment of *Plasmodium falciparum* merozoite surface protein 1 protects *Aotus* monkeys against malaria, Inf. Imm. 64, 253–261; Burghaus, P. A., Welide, B. T., Hall, T., Richards, R. L., Egan, A. F., Riley, E. M., Ripley-Ballou, W. and Holder A. A. (1996), Immunization of *Aotus nancymai* with recombinant C-terminus of *Plasmodium falciparum* merozoite surface protein 1 in liposomes and alum adjuvant does not induce protection against a challenge infection, Inf. Imm., in press.

Thus far, however, it has also been impossible to exclude other parts of gp190 on a rational basis as irrelevant to a protective immune response. Hence it is as necessary as ever to use the entire gene or the intact gp190 for vaccine investigations. Despite multiple investigations by various work-groups, however, there has not yet been any success in cloning and expressing the entire gp190/MSP1 gene.

Nor has it so far been possible to exclude a priori any part of the gp190 sequence as irrelevant to the protective immune response, so that it is as necessary as ever to use the entire gene or gene product for vaccine investigations. Nevertheless, despite many investigations by a number of working groups there has not yet been any successful cloning of the whole gene for gp190/MSP1.

One object of the present invention has consequently been to make available an adequate quantity of vaccine material in the form of the complete gp190/MSP1. It was a further object of the present invention to provide a process by which this vaccine material could be recovered.

In addition it was another object on the part of the present invention to provide a complete DNA sequence of gp190/MSP1 which could be expressed in a host organism.

Yet another object of the present invention was to provide host organisms containing the complete gp190/MSP1 gene.

Finally, it was also an object of the present invention to provide a stabilization process for AT-rich genes, as well as a stabilized gene suitable for expression characterized in a reduction of the AT content.

These objects are solved by the subject matter outlined in the claims.

In the following, certain concepts are explained in more detail in order to make clear how they should be understood in this context.

"Recombinant manufacturing process" means that a protein of a DNA sequence is expressed by a suitable host organism in which the DNA sequence has arisen from cloning and fusion of individual DNA fragments.

"Complete gp190/MSP1 protein" here means the entire gp190/MSP1 surface protein isolatable from the above named *Plasmodia*, especially *Plasmodium falciparum*, representing the main surface protein of the above named parasite as well as the proteins with analogous function from the other *Plasmodium* species such as *P. vivax*. The term therefore comprises in each case the main surface protein of the merozoites of the four malaria parasites named above as dangerous to man. "Complete gp190/MSP1 gene" means the gene coding for this protein. In this context "complete" signifies that the entire amino-acid sequence of the native protein is present or that the gene sequence codes for the entire amino-acid sequence of the native protein. Mutated and/or shortened forms of gp190/MSP1 are however included therewith insofar as they display the same immunization potential (vaccine protection) as the complete gp190/MSP1. Finally the term also includes variants of gp190/MSP1 characterized by containing in one molecule protein fragments of various alleles.

"FCB-1" is a strain of *P. falciparum* such as that described in Heidrich, H.-G., Miettinen-Baumann, A., Eckerskom, C. and Lottspeich, F. (1989) The N-terminal amino acid sequences of the *Plasmodium falciparum* (FCB1) merozoite surface antigens of 42 and 36 kilodalton, both derived from the 185–195-kilodalton precursor. Mol. Biochem. Parasitol. 34, 147–154.

"Attachment signal" here means a protein structure coded for by a DNA sequence at the 3' or 5' end of the gene according to the invention. Attachment signals are structures enabling the attachment of a polypeptide to other structures, such as for example membranes.

"Signal peptide" here signifies a protein structure for which a DNA sequence at the N-terminal end of the gene according to the invention codes. Signal peptides are structures which among other things enable penetration of the polypeptide into membranes.

In the context of the present invention "AT-content" means the percentage amount of adenine-thymine base pairs compared to guanine-cytosine base pairs.

"Cloning" will comprehend here all known state-of-the-art cloning methods which could be applied here, which are nevertheless not all described in detail because they belong among the normal tools of the person skilled in the art.

"Expression in an appropriate expression system" should here include all known state-of-the-art methods of expression in known expression systems which could be applied here, but which are nevertheless not all described in detail because they belong among the normal tools of the person skilled in the art.

It is a primary object in regard to the present invention that a process be provided by which the protein pg190/MSP1 and its gene can be produced in sufficient quantity without excessive cost.

This object is solved by the recombinant manufacturing process for preparing of the complete gp190/MSP1 protein of *Plasmodium*. In particular *Plasmodium falciparum* characterized in that the complete gene for gp190/MSP1 is expressed in a suitable system, preferably a host organism, by which a complete gp190/MSP1 gene and the protein coded by it are obtainable in sufficient quantities.

For the first time it is possible by this process to synthesize the protein in its entirety outside the parasite. As the analysis with conformational epitope-recognizing monoclonal antibodies shows, the protein thus synthesized is at least reproducibly synthesizable over wide areas in naturally folded form. By the recombinant manufacturing process many milligrams of intact gp190/MSP1 could in every case be recovered from the host organism, a quantity which for technical and economic reasons can never be recovered from parasites. Production of the protein in any desired quantity is now possible and opens new perspectives for its use as an experimental vaccine against malaria. Furthermore, the way is now open for the development of living vaccines as well as for vaccines based on nucleic acids.

Synthesis of the gene sequence coding for the protein gp190/MSP1 is preferentially based on the sequence of the FCB-1 strain of *P. falciparum*. *P. falciparum* is the agent of tropical malaria and hence of the most dangerous among the types of malaria. The basic gene is a representative of the "K1 allele", where K1 stands for a particular *P. falciparum* strain. Its coding sequence extends over 4917 base pairs and includes a signal sequence at the N-terminal end as well as an attachment sequence at the C-terminal end.

Furthermore, according to the invention the recombinant manufacturing process is preferentially characterized in having the AT content of the DNA sequence on which the protein is based reduced relative to the wild type, from 74% in the original gene preferably to about 55%, for example while the amino-acid sequence of the FCB-1 protein is maintained a DNA sequence with the codon frequencies usual in the human genome is produced. Other codon frequencies which reduce the AT content are also conceivable.

Preferentially the gene underlying the protein produced by the recombinant manufacturing process codes for the full amino-acid sequence including signal peptide and GPI attachment signal peptide, further described as gp190$^S$.

In another preferred embodiment, the gene on which the protein produced by the recombinant manufacturing process is based codes for the complete amino-acid sequence except for the GPI attachment signal. This embodiment is then described as gp190$^{S1}$.

In yet another preferred embodiment, the gene on which the protein produced by the recombinant manufacturing process is based codes for the complete amino-acid sequence except for the GPI attachment signal and the signal peptide. This embodiment is then described as gp190$^{S2}$.

In a further preferred embodiment type, the gene on which the protein produced by the recombinant manufacturing process is based codes for the complete amino-acid sequence and a trans-membrane attachment sequence.

In a particularly preferred embodiment the recombinant manufacturing process includes the following steps:

In the first place the design of the DNA sequence to be synthesized on the basis of the gene from *P. falciparum* FCB-1, in which a DNA sequence with for example the codon frequencies common in the human genome is manufactured with retention of the amino-acid sequence of the FCB-1 protein.

The AT content of the gene should be reduced by this, preferably to 55%. Further on in the process the planned sequence is divided for example into 5 overlapping regions, which at the same time correspond to domains of the natural processing products of gp190/MSP1 from FCB-1: p83, p31, p36, p30 and p19.

Desoxyoligonucleotides are synthesized, which in each case extend the entire length of a region.

The desoxyoligonucleotides so synthesized are particularly preferred where their sequence corresponds in an alternating manner to the "upper" (5'–3') or the "lower" (3'–5') DNA strand. The length of these oligonucleotides is preferably on average 120 nucleotides and they overlap the neighboring sequences in each case by about 20 bases.

In one possible embodiment DNA sequences of about double the length of the existing end-products are manufactured by asymmetrical PCR, in effect so that the superfluous DNA sequences nearby in each case represent the opposite strand. This leads in a second PCR amplification cycle to a second product corresponding to the length of four originally inserted oligonucleotides excluding the overlapping region. Transfer of these products to a preparation consisting predominantly of single-stranded DNA by asymmetrical PCR with the terminal oligonucleotides permits the manufacture in a further amplification step of an 800-bp long double-stranded DNA fragment in only 25 PCR cycles.

In this manner the regions coding for p19, p30, p36 and p31 are directly synthesized and molecularly cloned in *E. coli*. Clones with fault-free sequences are conserved either directly or by the joining up of fault-free sequence fragments. The region which codes for p83 is constructed by fusion from two sequences comprising about 1200 bp.

In the further course of production single sequences are cloned. As expression vectors candidates preferred are the plasmids pDS56, RBS11 ("Hochuli, E., Bannwarth, W., Doebeli, H., Gentz, R. and Stueber, D. (1988) Genetic approach to facilitate purification of recombinant proteins with a novel metal chelate adsorbent. Biotechn. 6, 1321–1325"), pBi-5 ("Baron, U., Freundlib, S., Gossen, M. and Bujard, H. (1995) Corregulation of two gene activities by tetracycline via a bidirectional promoter. Nucl. Acids Res. 23, 3605–3606") and ppTMCS. It is possible nonetheless also to conceive of other expression vectors.

Host organisms preferred for expression are *E. coli*, with the strain DH5alphaZ1 especially preferred (R. Rutz, Dissertation 1996, Heidelberg University), HeLa cells, CHO cells, *Toxoplasma gondii* (Pfefferkorn, E. R. and Pfefferkorn, C. C. 1976, *Toxoplasma gondii*:Isolation and preliminary characterization of temperature-sensitive mutants. Exp. Parasitol. 39, 365–376) or *Leishmania*. Additional host systems might be e.g. yeasts, baculoviruses or adenoviruses, so that the subject matter of the invention should not be limited to the host systems mentioned.

A further object of the present invention has been to provide a complete DNA sequence, suitable for expression, of the gp190/MSP1 surface protein of *P. falciparum*.

This object is solved by the complete DNA sequence, suitable for expression, of the gp190/MSP1 surface protein of *Plasmodium*, in particular *P. falciparum*, preferably obtainable through the recombinant process for preparing of the complete gp190/MSP1 protein of *Plasmodium*, in particular *Plasmodium falciparum* characterized in that the complete gene for gp190/MSP1 is expressed in a suitable system, preferably a host organism.

In a preferred embodiment of the present invention the sequence suitable for expression codes for the complete amino-acid sequence.

In another preferred embodiment of the present invention the sequence suitable for expression codes for the complete amino-acid sequence except for the attachment signal.

In a further preferred embodiment according to the present invention the DNA sequence suitable for expression codes for the complete amino-acid sequence except the attachment signal and the peptide signal. This embodiment of gp190/MSP1 can hence be characterized in including at the N-terminus 11 additional amino-acids, of which 6 are histidines.

Particularly preferred the DNA sequence suitable for expression contains no recognizable "splice-donor" and "splice-acceptor" sites, and is preferably characterized in not containing any larger GC-rich sequences which might result in stable hairpin structures at the RNA level.

Recognition signals for restriction enzymes which recognize sequences of six or more base pairs should preferably be avoided.

In a preferred embodiment specific cleavage sites for restriction endonucleases, occurring only once in the gene, are introduced into regions to separate the existing domains following processing of the protein.

Particularly preferred would be the presence at both ends of the gene of sequences for restriction endonucleases which do not occur in the gene.

Furthermore host organisms containing the complete sequence of gp190/MSP1 surface protein are provided by the invention.

Such host organisms are preferably *E. coli*, particularly preferred being the strain DH5alphaZ1, HeLa cells, CHO cells, *Toxoplasma gondii* or *Leishmania*. The HeLa and CHO cells ought preferably to synthesize constitutively tTA.

Finally the present invention provides a possibility of using a gp190/MSP1 surface protein created produced according to the recombinant manufacturing process, or parts thereof, for active immunization against malaria.

The scheme for synthesis presented here also permits manufacture of the second allele of the gp190/MSP1 gene, whereby the dimorphism of the protein is also taken into account. The main variability of the protein depends however on the sequences of two relatively short blocs, blocks II and IV (ref. 1), which are oligomorphic. The present sequence data make it possible to disclose over 95% of all known gp190/MSP1 sequences with 6–8 sequence combinations of these blocs. The synthesis of these sequence variants can be brought about problem-free by means of the strategies proposed here, so that variants can be built up both in the K1 and in the MAD20 allele. Vaccines from the families of sequences thus created can confer protection where required against a wide spectrum of parasites with gp190/MSP1 variants.

The manufacture of different types of vaccine is possible:

At the level of protein preparations, where in each instance mixtures of the two families (K1 type, MAD20 type with different variants of Blocs II and IV) can come into use. Various carrier or adjuvant materials could be added: aluminum oxide, liposomes, IscomsQSz1, etc.

At the level of live vaccines: (a) viral carriers, especially vaccinia and adenoviruses; (b) parasites as carriers, particularly avirulent forms of *Leishmania* and *Toxoplasma*; (c) bacterial carriers, e.g. *Salmonella*.

At the level of nucleic acids, whereby for example vectors suitable for gene therapy would be used to introduce the gene into the host; beyond that the introduction of nucleic acids coding for the desired protein can be envisaged.

A further possibility for vaccination lies in the use of a gp190/MSP1 protein produced according to the recombinant manufacturing process set out by the invention, for the production of monoclonal antibodies which can then be used in their turn for passive immunization against malaria.

Similarly it becomes possible to use the DNA sequence on which the protein is based at an intermediate stage arising in the course of the recombinant manufacturing process for the construction of a vaccine based on nucleic acids.

Finally the invention also concerns a process for the stabilization of gene sequences, especially for sequences which do not show adequate stability in expression systems.

According to the invention this stabilization is attained because the AT content of the sequence is reduced.

Moreover a stabilized gene characterized by having a reduced AT content is provided by the invention. An example of such a stabilized gene is the gene for gp190/MSP1 surface protein according to the present invention.

In the following the invention will be described with the help of figures and tables as well as some examples in individual embodiments.

They show:

FIG. 1: Schematic representation of the gp190/MSP1 precursor protein from *P. falciparum* (FCB-1).

FIG. 2: Two vaccine trials carried out on *Aotus* monkeys with native gp190/MSP1 from *P. falciparum* (FCB-1).

Figure 2A:
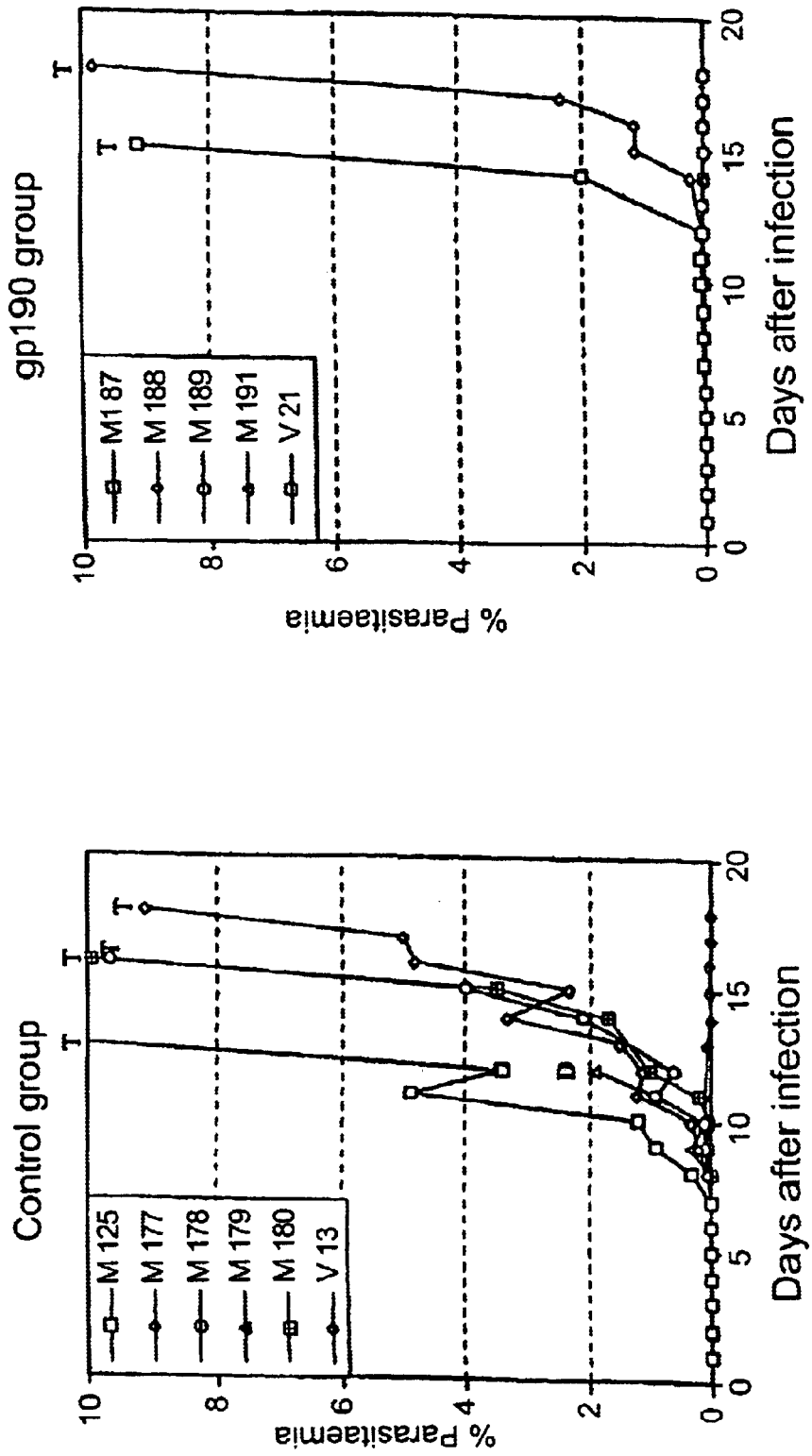

FIG. 2A: With 3×60 micrograms gp190/MSP1

Figure 2B:
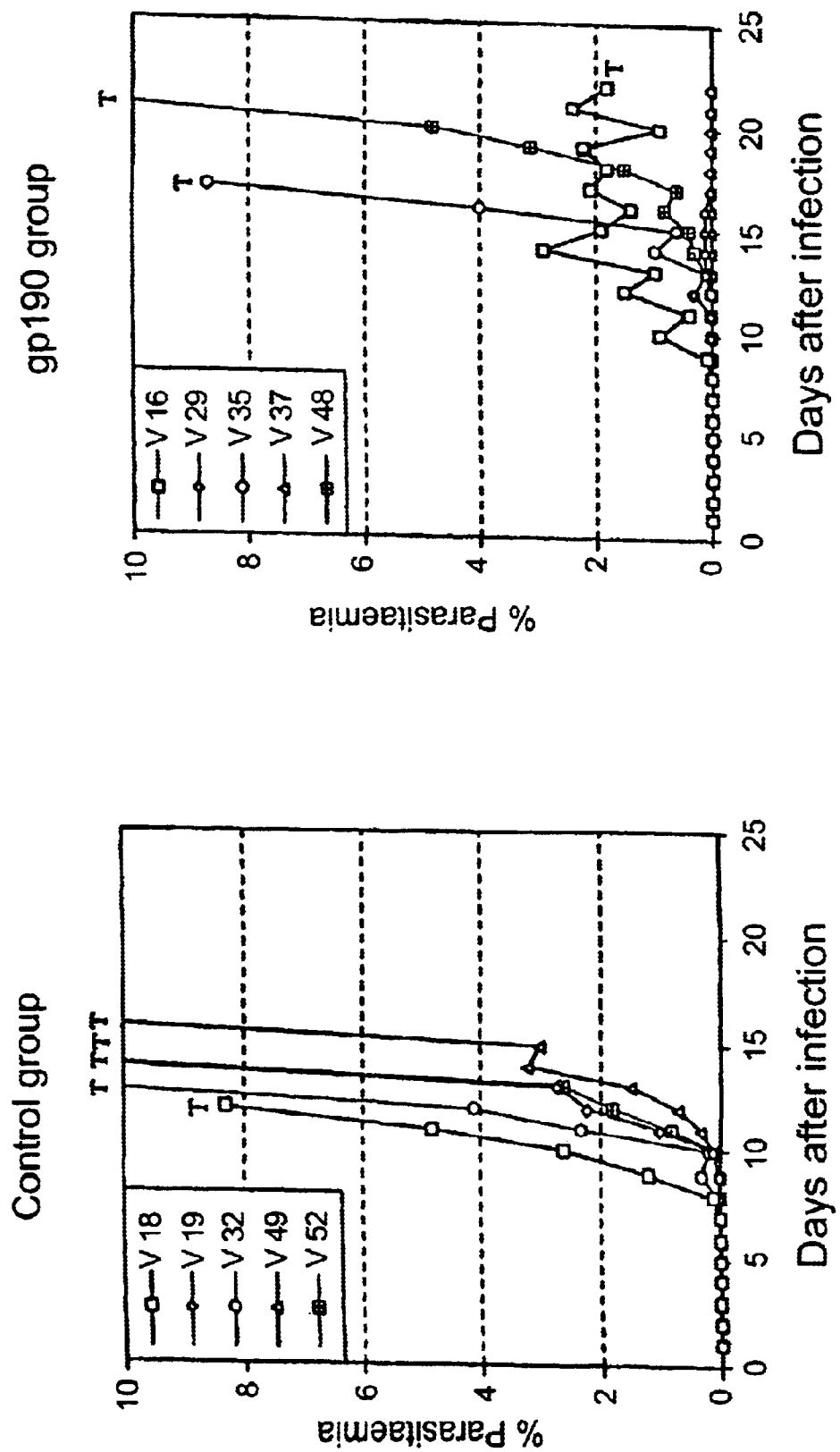

FIG. 2B: With 3×40 micrograms gp190/MSP1

Figure 3A:
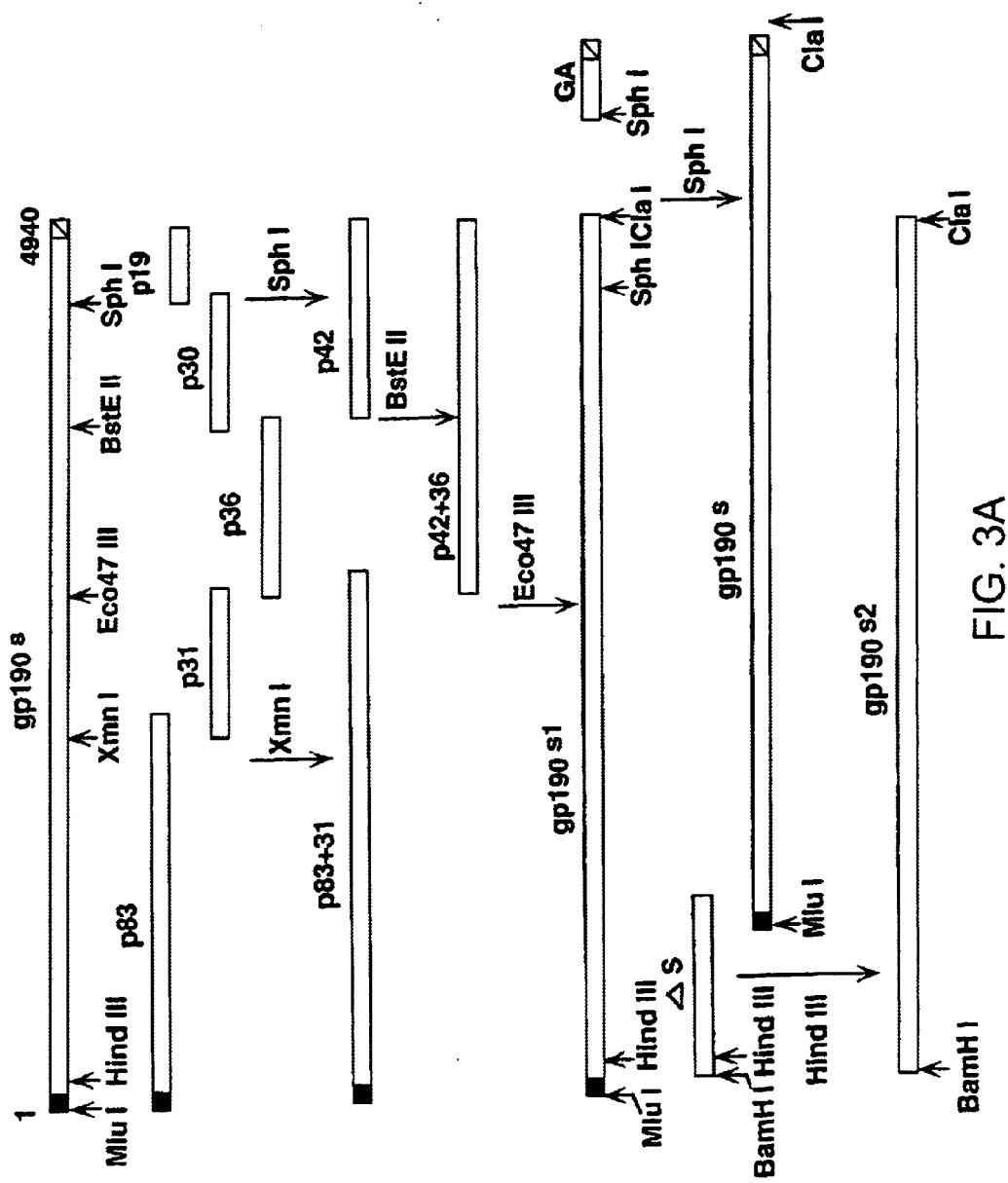

FIG. 3A: Strategy of synthesis of the gp190/MSP1 gene

Figure 3B:
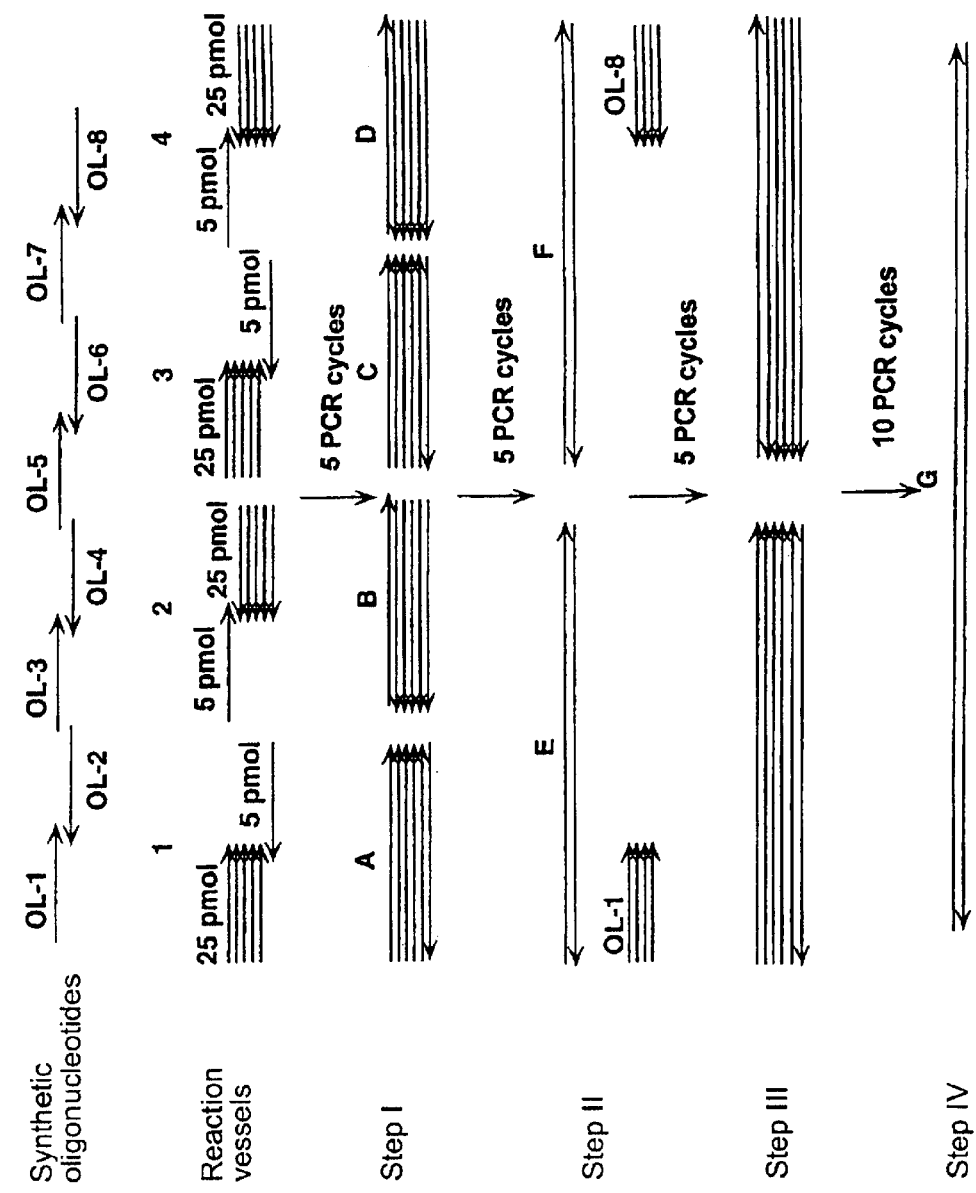

FIG. 3B: Principle of PCR-based total synthesis

FIGS. 3C–3X: Total sequence of gp190$^S$

FIG. 3Y: N- and C-termini of gp190$^{S1}$ variant

Figure 4A:
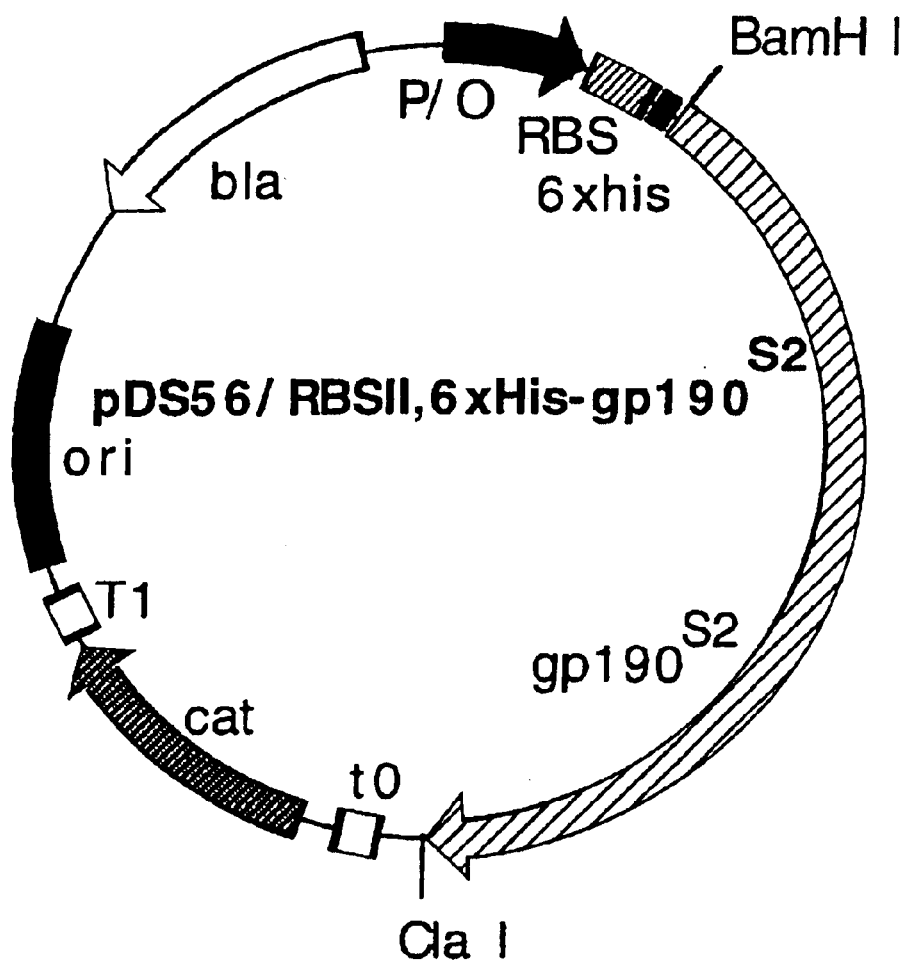

FIG. 4A: Expression vector pDS56 with gp190$^{S2}$ sequence

Figure 4B:
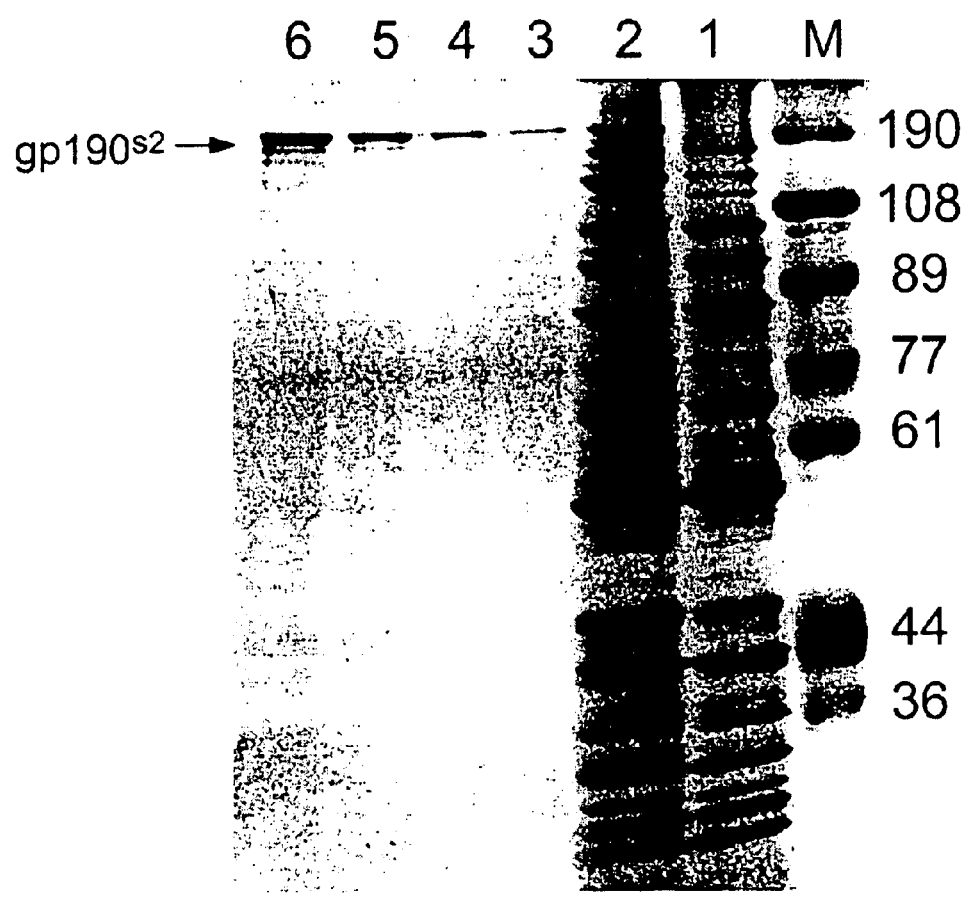

FIG. 4B: Gel electrophoresis of gp190$^{S2}$

Figure 5A:
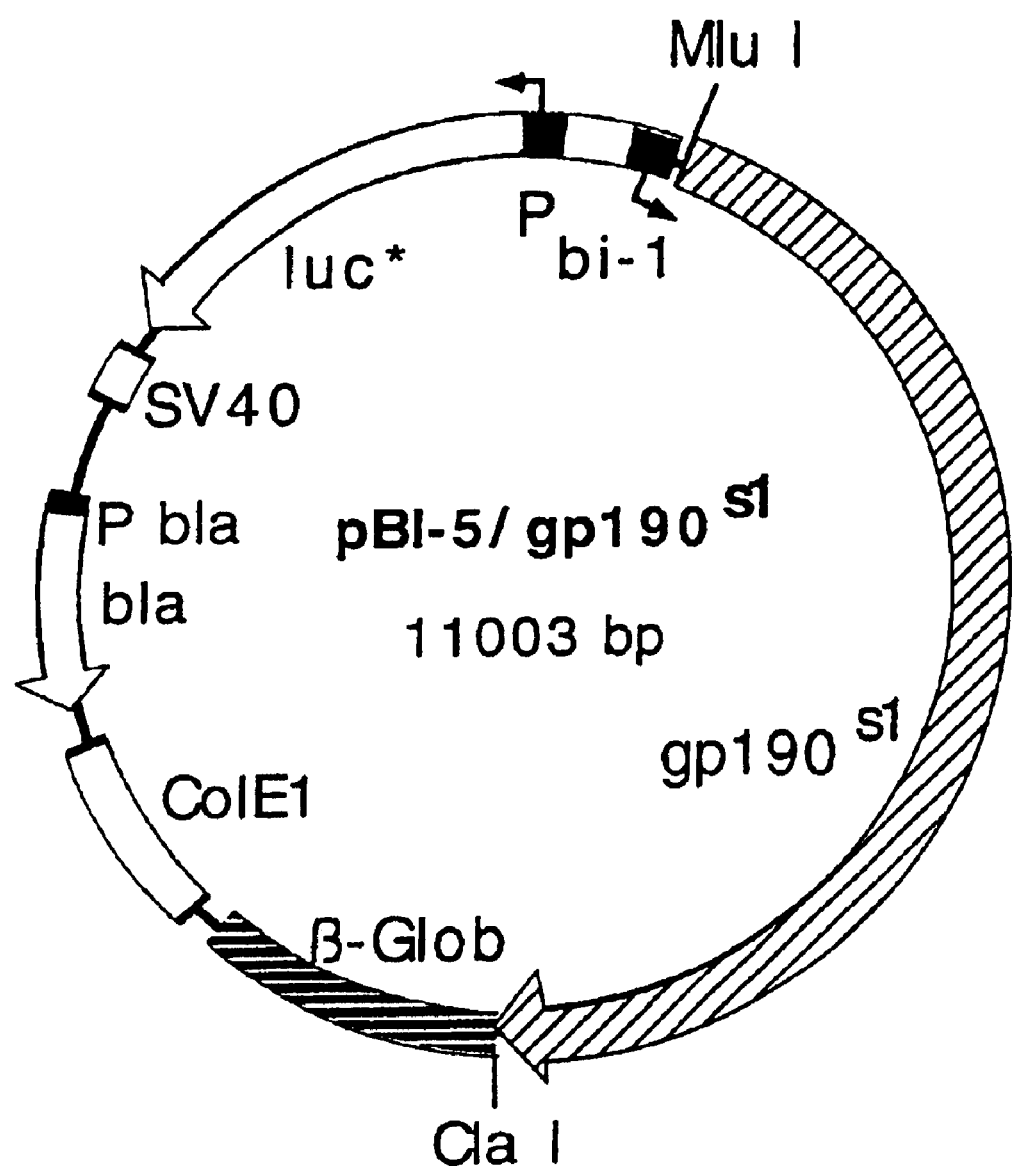

FIG. 5A: Expression vector pBi-5 with gp190$^{S1}$ sequence

Figure 5B:
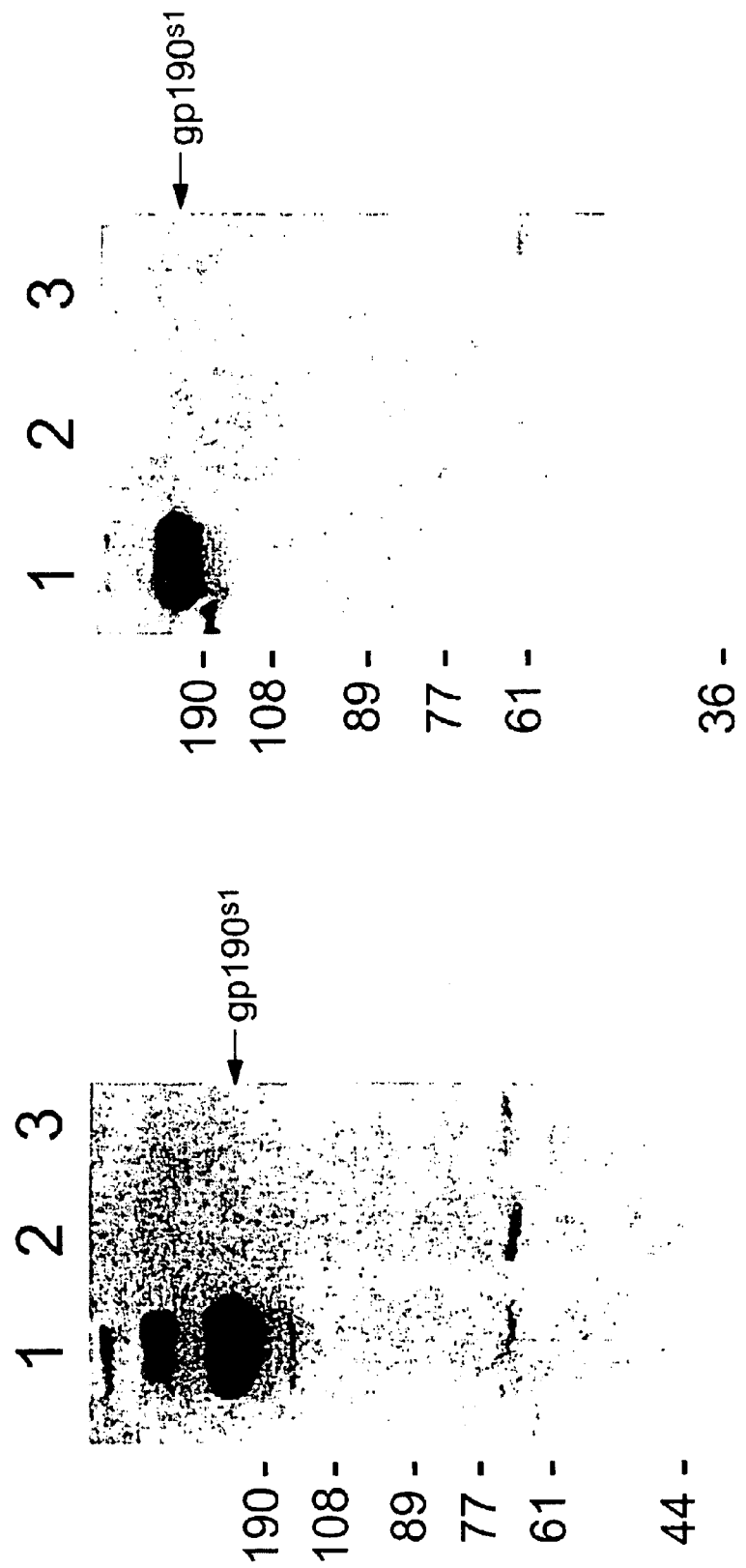

FIG. 5B: Immunofluorescence of HeLa cells

FIG. 5C: Electrophoretic characterization of gp 190$^{S1}$ purified from HeLa cells.

Figure 6A:
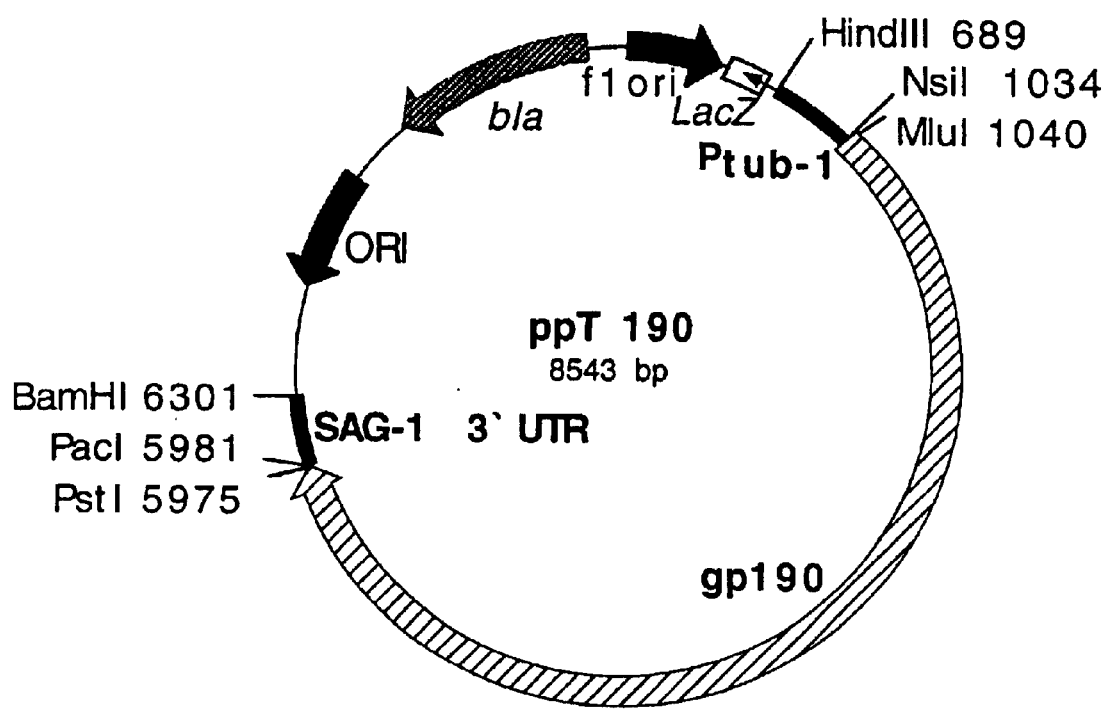

FIG. 6A: Expression vector ppT 190 with gp190 sequence

FIG. 6B: Polyacrylamide gel electrophoresis of gp 190 from *T. gondii*.

FIG. 6C: Polyacrylamide gel electrophoresis of gp190 from *T. gondii*

In the gp190/MSP1 precursor protein from *P. falciparum* schematically represented in FIG. 1 the dark blocs stand for regions which are strongly conserved in all strains. The cross-hatched blocs indicate the dimorphic areas, which in the case of the FCB-1 isolate derive from the K1 allele. O1 and $O_2$ indicate the oligomorphic areas. S denotes the peptide signal sequence containing 19 amino-acids, GA the C-terminal region, which includes the signal for the GPI attachment of the protein to the membrane. The arrows indicate the sites of the processing by which the proteins p53, p31, p36, p30 and p19 arise. The gp190 gene codes for altogether 1639 amino-acids.

The other figures are more conveniently explained in the context of the following Examples.

EXAMPLES

Example 1

Figure 3T:
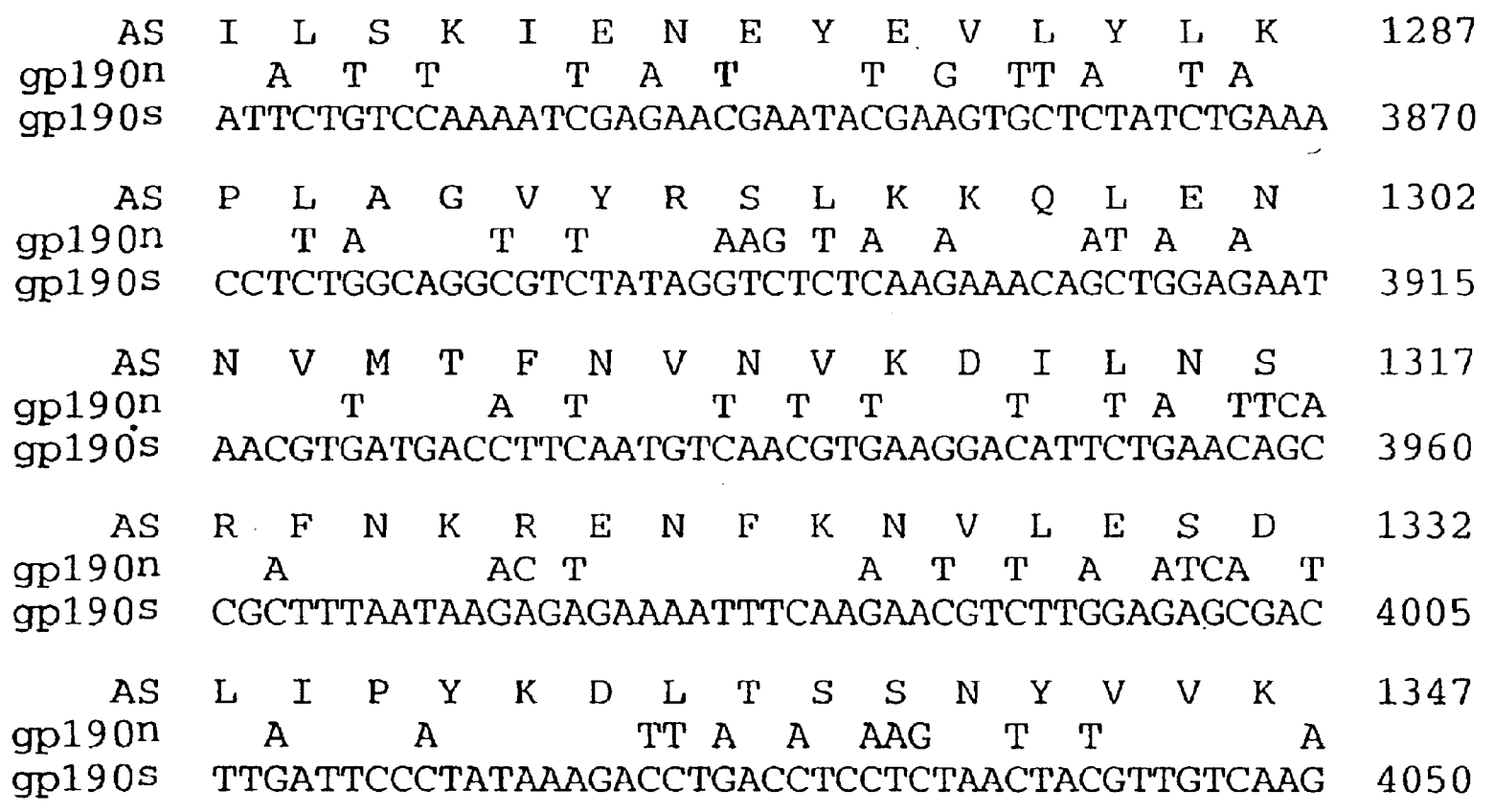

Total Synthesis of One of the DNA Sequences Coding for gp190/MSP1 (see FIG. 3)

A. Strategy of Synthesis of the gp 190/MSP1 Gene (gp190$^S$) (see FIG. 3A).

The sequence was divided into fragments corresponding to the main processing products: p83, p31, p36, p30 and p19. In the transition regions cleavage sites for restriction endonucleases (arrows in FIG. 3) were inserted in such a way that the amino-acid sequence was not altered. All the particular cleavage sites are found only once in the sequence.

The fragments were synthesized to overlap, so that the cleavage sites at the respective ends made attachment by ligation to the neighboring fragment possible. All individual fragments contain in addition at their 5' ends a BamHI division site for insertion into expression vectors. The entire sequence could be cloned via MluI and ClaI. The scheme indicated here leads in addition to a sequence which cannot produce the GPI attachment since the C-terminal lacks 18 amino-acids. Synthesis of a corresponding oligonucleotide as well as of a "primer" extending over the SphI cleavage site, leads after PCR to the GA fragment which could be used by SphI and ClaI, the resulting total sequence being gp190$^S$. On removing the sequence coding for the peptide signal, "PCR Primer" is produced, over which the fragment AS has been synthesized. It is permissible to alter the N-terminal via a BamHI and a HindIII cleavage site in such a way that the protein begins with amino-acid no. 20. The nuclear sequence which encodes gp190/MSP1 without signal sequence and without GPI attachment signal was designated gp190S2. Deletion of the GPI attachment signal alone leads to gp190$^{S1}$.

B. Principle of the PCR-supported Total Synthesis (see FIG. 3B)

Oligodesoxynucleotides of about 120 nucleotides have been synthesized in an alternating manner from the coding or the non-coding strand in such a way that in each case about 20 bases overlapped with the neighboring fragment. The scheme illustrates for example the synthesis of a fragment about 800 bp long from oligonucleotides. At the first stage 2 oligonucleotides were amplified "asymmetrically" in each of 4 reaction vessels. This resulted in 4 populations of DNA about 220 bp in length, consisting predominantly of single strands (A, B, C, D). Uniting A to B and C to D with amplification over 5 cycles led to 2 approximately 400 bp long double-stranded products. Asymmetrical amplification of these DNA fragments (Stage III) resulted in single-stranded populations which following uniting and amplification (Stage IV) resulted after 10 cycles in the end-product G of about 800 bp in length. This synthesis could be carried out without isolation of intermediate products and without renewing buffer or enzyme, and was completed in 3 hours. The end-product was purified electrophoretically, divided up with the appropriate restriction endonucleases, and cloned in E. coli in pBluescript (Stratagene), to which polylinker a MluI and a ClaI cleavage site had been added.

C. Total Sequence of gp190$^S$ (See FIGS. 3C–3X)

Following fusion of all part sequences (FIG. 3A) in pBluescript, the sequence of the gene was checked by the di-deoxy method. The reading frame of gp190$^s$ had a length of 4917 bp (+2 stop-codons) and encoded an amino-acid sequence corresponding to that of the gp190/MSP1 from FCB-1 (1639 amino-acids).

D. N- and C-termini of gp190$^{S1}$ Variant (see FIG. 3Y)

The N-terminal and C-terminal sequences of gp120$^{S1}$ are provided as SEQ ID NO:4 and SEQ ID NO:5, respectively. FIG. 3D depicts nucleotides 1–17 and 4863–4894 of SEQ ID NO:4 and amino acids 1–3 and 1619–1621 of SEQ ID NO:5. The N-terminal sequence of gp120$^{S2}$, beginning with the BamHI cleavage site, indicates the transition at amino-acid 20, from which it can be assumed that after splitting of the signal peptide it defines the N-terminus. At the C-terminus the sequence encoded ended at amino-acid 1621. The stop-codon followed the ClaI cleavage site. The nucleotide and amino acid sequences of gp120$^{S2}$ are provided as SEQ ID NO:6 and SEQ ID NO:7, respectively. FIG. 3D depicts nucleotides 1–17 and 4806–4838 of SEQ ID NO:6 and amino acids 1–3 and 1600–1602 of SEQ ID NO:7.

Example 2

Expression of gp190$^{S2}$ in E. coli

A. Expression vector (see FIG. 4A)

The gp120$^{S2}$ sequence was inserted via the BamHI and ClaI cleavage sites into pDS56RBSII, by means of which 6 histidine as well as some amino-acids originating in the vector were fused to the N-terminus. This produces the following N-terminal sequence on the reading-frame:

MetArgGlySer(His)$_6$GlySer (SEQ ID NO:8). Through the promoter P$_{N251acO-1}$ the transcription comes under lacR/O/IPTG control.

B. Expression and Purification of gp190$^{S2}$ (see FIG. 4D)

Carrying over the vector pDS56RBSIIgp190$^{S2}$ into E. coli DH5alphaZ1 and induction of a synthesis through IPTG resulted after electrophoretic separation of the total protein extract from the culture in a clearly visible band of the anticipated size (arrow). Purification of the material through IMAC and affinity chromatography (antibody column with mAK5.2) led to a homogeneous product of about 190 kD. In the Figure M stands for molecular weight standards; 1=E. coli before; 2=after induction with IPTG for 2 hours; 3, 4, 5=fractions from elution of the mAK column.

Example 3

Tetracycline-Controlled Expression of gp190$^{S1}$ in Hela and CHO Cells and Isolation of the _Product (See Also FIGS. 5 and 6b)

A. The gp190 sequence was inserted via the BamHI/ClaI cleavage sites into the expression vector pBi-5. In this way transcription of the gene came under the control of a bidirectional "tTA-reponsive" promoter and could be regulated through Tc. The bidirectional promoter simultaneously initiated transcription of the indicator gene luciferase. In consequence the regulation of the expression could easily be followed (see also FIG. 5A).

B. Immunofluorescence of HeLa Cells, Which Express Luciferase and gp190$^{S1}$ Under Tc Control The production of luciferase (left), gp190$^{S1}$ (middle) in the absence of Tc was demonstrated in HITA93–9 cells, which contain the bidirectional transcription unit of (A). Following addition of Tc no noteworthy synthesis of gp190S1 was shown.

C. Electrophoretic Characterization of gp190$^{S1}$ Purified from HeLa Cells

The HeLa cell clone HtTA93-9 as well as the CHO cell clone CHO27-29 have been cultivated with or without Tc. Ce3ll Cell extracts separated by electrophoresis have been analyzed with mAK5.2 by means of "Western blotting" (FIG. 5B); analysis of the CHO cell line is shown on the left, of HeLa on the right. (1)=culture without, (2)=culture with Tc, (3)=non-transfected HtTA-1 cell line. Molecular weight standards are in each case indicated on the left.

D. Purification of gp190$^{S1}$ Synthesised by HeLa Cell Clone HtTA93-9

Preparative cultivation of the HtTA line and induction of expression of gp190$^{S1}$ by withholding Tc permitted isolation of the gene product by affinity chromatography (mAK5.2 column).

The polyacrylamide gel stained with Coomassie (FIG. 6B) following electrophoresis displayed a product consisting of gp190$^{S1}$ as well as another protein of about 50 kD. The latter was not derived from gp190$^{S1}$ and thus originated from the HeLa cells. Its projected removal should nevertheless present no difficulty in principle.

Example 4

Expression of gp190$^{S1}$ in *Toxoplasma gondii* and Purification of the Product (See also FIG. 6).

A. The gp190$^{S}$ sequence was inserted into the vector ppT via MluI/PstI. This brought the gene under the control of the tubulin promoter ($P_{tub-1}$) of *T. gondii*. The 3' untranslated region (VTR) originated from the main surface protein of *T. gondii* (SAG-1).

B. Expression of gp190$^{S}$ in *T. gondii*

Transfection of *T. gondii* with pTT190 led to the isolation of parasite lines which expressed constitutively gp190$^{s}$. Immunofluorescence with mAK5.2 showed not only expression of the gene but also situated the binding of the expression product close to the surface of the parasite, since it, like SAG-1, provokes the same pattern of immunofluorescence.

C. Isolation of gp190S from *T. gondii.*

By means of affinity chromatography (mAK5.2 column) gp190$^{S}$ was purified from a prepared quantity of *T. gondii* ($5\times10^9$ parasites). The extremely pure protein possessed the anticipated molecular weight, as the Coomassie-stained polyacrylamide gel indicated following electrophoresis (2–3 on FIG. 6B). At no. (1) on FIG. 6C purified gp 190$^{S1}$ from CHO cells is represented with molecular weight marked on the left side.

Example 5

Characterization of gp190$^{S}$ with Monoclonal Antibodies.

The interaction of 16 monoclonal antibodies with gp190$^{S}$ from the various heterologous expression systems was reviewed by immunofluorescence on *P. falciparum* and *T. gondii* or by "Western blot" on the purified proteins. Complete agreement was found when the two parasites were compared (number of +s indicates the relative intensity of the fluorescence). On Western blotting 12 mAKs reacted with gp190$^{s}$ from *E. coli* and *T. gondii*. On the other hand 3 antibodies did not bind to material isolated from CHO cells. Antibodies 15 and 16, which recognize epitopes from the oligomorphs or the alternative allele (MAD20), did not react. The results are summarized in Table 1, in which ND means "not carried out".

Example 6

Expression of gp190$^{S}$ in Heterologous Systems

1. Expression in *E. coli*

The gp190$^{S2}$ was inserted into the expression vector pDS5B, RBSII, where it came under control of the promoter $PN_{251acO-1}$, which can be controlled via the lac operator/repressor/IPTG system (FIG. 4A). Transfer of the plasmid into repressor-producing *E. coli* cells, eg *E. coli* DH5alphaZ1, permitted expression of pg190$^{S2}$ under IPTG control. By means of a nickel-chelate column the raw product could be isolated via the N-terminal $(His)_6$ sequence introduced by the vector. An ensuing affinity chromatography on an antibody column led to an extremely pure preparation. Since the monoclonal antibodies used (mAK5.2) recognized a conformational epitope in the C-terminal region, this 2-step purification selected a full-length intact protein with correct folding at least at the C-terminus (FIG. 4B).

In contradistinction to the natural material the end-product possesses 11 additional amino-acids at the N-terminus, of which 6 are histidines. It contains no N-terminal signal and also no C-terminal attachment sequence. The *P. falciparum*-specific sequence begins with amino-acid 20 and ends with amino-acid 1621.

2. Controlled Expression of gp190$^{S1}$ in HeLa and CHO Cell Cultures

The gp190S1 was inserted into the vector pBi-5 and thereby placed under control of a promoter regulable by tetracycline (Tc). The Tc-controlled system was chosen for 2 reasons:

- It belongs to the expression systems with which the highest yield is obtained in mammalian cells.
- Unsecreted foreign proteins at high concentration can interfere negatively with cell metabolism. Synthesis of the desired product is consequently begun only after maturation of the culture.

In the construct pBi5-gp190$^{S}$ a bidirectional promoter was activated by the Tc-controlled transcription activator and initiated transcription of both gp190$^{S1}$ and the luciferase indicator gene. In the presence of Tc the promoter is inactive. The transcription unit was transferred into both HeLa and CHO cells, which both synthesize constitutively tTA (HtTA line: Gossen, M. and Bujard, H. (1992), Tight control of gene expression in mammalian cells by tetracycline-responsive promoters. Proc. Natl. Acad. Sci. USA 89, 5547–5551; CHO-tTA line, unpublished). Through cotransfection ($Ca^{2+}$-phosphate method) with a hygromycin-resistance-inducing marker gene was selected for successful chromosomal integration. Hygromycin-resistant clones were then investigated for regularity of the expression>Tc, in which luciferase activity was used as indicator. The gp 190 synthesis was tested in well regulable clones (regulation factor·Tc 1000). Immunofluorescence analysis as well as investigation by "Western blot" (FIG. 5B) allowed the identification in both cell types of clones which synthesized gp190 under strictly regulable conditions. The best regulable of 20 clones were in each case subcloned. The subclones HtTA93-9 and CHO27–29 were used for cultures on a scale of 10:1. From cell extracts of these cultures intact gp190$^{S1}$ could be isolated by means of affinity chromatography (mAK5.2). The material was homogeneous except for a single cellular component which did not derive from gp190$^{S1}$ and made up 25% of the preparation (FIG. 6B). It had to be removed in a further purification step.

3. Expression of gp190S in *Toxoplasma gondii.*

Like *P. falciparum, Toxoplasma gondii* belongs to the *Apicomplexa* and consequently has a protein modification system apparently similar to that of *P. falciparum. T. gondii* can be transfected with foreign DNA which is efficiently integrated into the genome and furthermore allows problem-free multiplication of *T. gondii* in cell culture. To obtain a product most like native gp190, gp190S2 is expressed in such a way that the protein is secreted on the surface of the parasite and, as in *P. falciparum*, bound to the membrane via a GPI analogue. In that way the gp190S2 (FIG. 3A) has been inserted (FIG. 6A) into the plasmid ppTMCS (D. Soldati, unpublished) and thereby placed under the control of the *T. gondii* tubulin promoter.

This expression construct was transfected into *T. gondii*. Selection with chloramphenicol led to resistant clones synthesizing gp190 which were detected by immunofluorescence.

The immunofluorescence with anti-gp190 antibodies was indistinguishable from a corresponding pigmentation of the parasites by means of antibodies against SAG1, the main surface protein of *T. gondii*. It may be deduced from this that gp190 is bound to the surface of *T. gondii*. Several *T. gondii* clones (Nos. 3.1 to 3.4) were characterized and saved for the production of gp190. Using affinity chromatography (mAK5.2) gp190 was isolated from *T. gondii* cultures (clone 3.4) cultivated on a preparative scale. Electrophoretic analysis revealed a homogeneous product with a migration rate similar to that of the intact protein (FIG. 6B).

Example 7

Characterization of gp190 Protein from Various Expression Systems by Means of Monoclonal Antibodies.

A set of gp190-specific monoclonal antibodies, of which a number recognize conformational epitopes, were used to compare the reactivity of the antibodies with *P. falciparum* and *T. gondii* parasites via immunofluorescence. Table 1 shows that the reactvity of the 16 antibodies with either parasite is the same. This is a strong indication that in *T. gondii* "native" gp190 is being mostly produced. Comparison of the reactivity of the antibodies with protein from *E. coli*, HeLa or CHO cells as well as T gondii shows also that most of the antibodies react with the 4 preparations. In particular the protein derived from *E. coli* recognizes more of the antibodies than that produced in mammalian cells. This is apparently a consequence of glycosylation in mammalian cells.

Example 8

Immunization of *Aotus lemurinus griseimembra* monkeys with gp190/MSP from *P. falciparum* (FCB-1).

Two independent immunization experiments (A, B) were carried out. In them in one instance (A) 1.0 mg and in the other (B) 0.6 mg of very pure gp190/MSP1 was extracted from about $2 \times 10^{11}$ parasites respectively.

The protein was administered together with Freund's Adjuvant (FCA). The control group received only FCA. Immunization equally with the protein mixture or the adjuvant was done three times at intervals of 4 weeks. Two weeks after the last immunization each of the animals was infected with $10^5$ parasites (FVO strain) from a donor animal. Parasitaemia was measured daily. The results are summarized in FIG. 2. The symbols mean:

T: that the animals were treated with resochin

D: a dead animal

FIG. 2A: individuals in the vaccinated group each received 3×60 micrograms gp190/MSP1

FIG. 2B: individuals in the vaccinated group each received 3×40 micrograms gp190/MSP1

While in the control group only 1/11 animals did not develop parasitaemia, this was 6/10 in the vaccinated group. The four animals in the vaccinated group who did develop a pronounced parasitaemia did so—in comparison to the control group—with an average delay of four days (exceeding the 2% limit of parasitaemia).

These experiments indicate for the first time a highly significant protection by gp190/MSP1 against infection with *P. falciparum* in a monkey model. The process according to the invention consequently permits a practical vaccine against malaria to be presented for the first time.

TABLE 1

Interaction of gp 190$^s$ with monoclonal antibodies

| | | | | IFA | | | Western blot | |
|---|---|---|---|---|---|---|---|---|
| Code | mAb | Type of epitope | Variability | P.f. FCB | Toxoplasma | E. coli | Toxoplasma | CHO |
| 1 | 5.2 | conformational | conserved | ++++ | ++++ | + | + | + |
| 2 | 12.10 | conformational | conserved | ++++ | ++++ | + | + | + |
| 3 | 7.5 | conformational | conserved | ++++ | ++++ | + | + | + |
| 4 | 12.8 | conformational | conserved | ++ | ++ | + | + | + |
| 5 | 7.3 | conformational | dimorph (K1) | ++++ | +++ | + | + | + |
| 6 | 2.2 | conformational | conserved | ++++ | ++++ | + | + | + |
| 7 | 7.6 | conformational | dimorph (K1) | ++++ | ++++ | + | + | + |
| 8 | 9.8 | conformational | conserved | ++++ | ++ | + | + | − |
| 9 | 13.2 | sequential | conserved | ++++ | ++++ | + | + | + |
| 10 | 13.1 | sequential | dimorph (K1) | ++++ | +++ | + | + | − |
| 11 | 6.1 | sequential | dimorph (K1) | ++++ | ++++ | + | + | ND |
| 12 | A5Z | unknown | unknown | +++ | +++ | + | + | + |
| 13 | 17.2 | unknown | unknown | ++++ | +++ | ND | ND | ND |
| 14 | 15.2 | unknown | unknown | ++++ | +++ | ND | ND | ND |
| 15 | 9.7 | conformational | dimorph (MAD20) | − | − | − | − | − |
| 16 | 12.1 | sequential | oligomorph | − | − | − | − | − |

What is claimed is:

1. A method for producing a merozoite surface protein-1 (MSP-1) of a *Plasmodium*, wherein the MSP-1 protein has a molecular weight in a range of 190 kD to 220 kD, and wherein the MSP-1 protein has a signal peptide and an attachment signal, the method comprising expressing a nucleotide sequence encoding the MSP-1 protein in a single expression vector, wherein the adenine and thymine (AT) content of the expressed nucleotide sequence encoding the MSP-1 protein is less than the AT content of the corresponding naturally occurring nucleotide sequence encoding the MSP-1 protein.

2. The method of claim 1, wherein the *Plasmodium* is a strain of *Plasmodium falciparum*.

3. The method of claim 2, wherein the strain of *Plasmodium falciparum* is *P. falciparum* strain PFB-1.

4. The method of claim 1, wherein the AT content of the expressed nucleotide sequence is reduced from about 74% to about 55%.

5. The method of claim 1, wherein the expressed nucleotide sequence encoding the MSP-1 protein is set forth in SEQ ID NO:2.

6. The method of claim 1, wherein the expressed nucleotide sequence encodes an MSP-1 protein having the amino acid sequence consisting of amino acids 1–1639 of SEQ ID NO:3.

7. The method claim 1, wherein the expressed nucleotide sequence is expressed in an *Escherichia coli* (*E. coli*) strain.

8. The method of claim 7, wherein the *E. coli* strain is DH5alphaZ1.

9. The method of claim 1, wherein the expressed nucleotide sequence is expressed in an expression system selected from the group consisting of HeLa cells and CHO cells.

10. The method of claim 1, wherein the expressed nucleotide sequence is expressed in an expression system selected from the group consisting of *Toxoplasma gondii* and *Leishmania*.

11. A method for producing a merozoite surface protein-1 (MSP-1) protein of a *Plasmodium*, wherein the MSP-1 protein has a molecular weight in a range of 190 kD to 220 kD, and wherein the MSP-1 protein lacks an attachment signal, the method comprising expressing a nucleotide sequence encoding the MSP-1 protein in a single expression vector, wherein the adenine and thymine (AT) content of the expressed nucleotide sequence encoding the MSP-1 protein is less than the AT content of the corresponding naturally occurring nucleotide sequence encoding the MSP-1 protein.

12. The method of claim 11, wherein the *Plasmodium* is a strain of *Plasmodium falciparum*.

13. The method of claim 12, wherein the strain of *Plasmodium falciparum* is *P. falciparum* strain PFB-1.

14. The method of claim 11, wherein the AT content of the expressed nucleotide sequence is reduced from about 74% to about 55%.

15. The method of claim 11, wherein the expressed nucleotide sequence encodes an MSP-1 protein having the amino acid sequence consisting of amino acids 1–1621 of SEQ ID NO:3.

16. The method claim 11, wherein the expressed nucleotide sequence is expressed in an *Escherichia coli* (*E. coli*) strain.

17. The method of claim 16, wherein the *E. coli* strain is DH5alphaZ1.

18. The method of claim 11, wherein the expressed nucleotide sequence is expressed in an expression system selected from the group consisting of HeLa cells and CHO cells.

19. The method of claim 11, wherein the expressed nucleotide sequence is expressed in an expression system selected from the group consisting of *Toxoplasma gondii* and *Leishmania*.

20. A method for producing merozoite surface protein-1 (MSP-1) of a *Plasmodium*, wherein the MSP-1 protein has a molecular weight in the range of from 190 kD to 220 kD, and wherein the MSP-1 protein lacks a signal peptide and an attachment signal, the method comprising expressing a nucleotide sequence encoding the MSP-1 protein in a single expression vector, wherein the adenine and thymine (AT) content of the expressed nucleotide sequence encoding the MSP-1 protein is less than the AT content of the corresponding naturally occurring nucleotide sequence encoding the MSP-1 protein.

21. The method of claim 20, wherein the *Plasmodium* is a strain of *Plasmodium falciparum*.

22. The method of claim 21, wherein the strain of *Plasmodium falciparum* is *P. falciparum* strain PFB-1.

23. The method of claim 20, wherein the AT content of the expressed nucleotide sequence is reduced from about 74% to about 55%.

24. The method of claim 20, wherein the expressed nucleotide sequence encodes an MSP-1 protein having the amino acid sequence consisting of amino acids 20–1621 of SEQ ID NO:3.

25. The method claim 20, wherein the expressed nucleotide sequence is expressed in an *Escherichia coli* (*E. coli*) strain.

26. The method of claim 25, wherein the *E. coli* strain is DH5alphaZ1.

27. The method of claim 20, wherein the expressed nucleotide sequence is expressed in an expression system selected from the group consisting of HeLa cells and CHO cells.

28. The method of claim 20, wherein the expressed nucleotide sequence is expressed in an expression system selected from the group consisting of *Toxoplasma gondii* and *Leishmania*.

* * * * *

UNITED STATES PATENT AND TRADEMARK OFFICE
CERTIFICATE OF CORRECTION

| | |
|---|---|
| PATENT NO. | : 6,933,130 B1 |
| APPLICATION NO. | : 09/269874 |
| DATED | : August 23, 2005 |
| INVENTOR(S) | : Bujard, Hermann et al. |

It is certified that error appears in the above-identified patent and that said Letters Patent is hereby corrected as shown below:

The title of the application should read:

--"RECOMBINANT PROCESS FOR PREPARING A COMPLETE MALARIA ANTIGEN GP190/MSP1"--

Signed and Sealed this

Fifteenth Day of August, 2006

JON W. DUDAS
*Director of the United States Patent and Trademark Office*

SEQUENCE LISTING

<160> NUMBER OF SEQ ID NOS: 8

<210> SEQ ID NO 1
<211> LENGTH: 4920
<212> TYPE: DNA
<213> ORGANISM: Plasmodium falciparum

<400> SEQUENCE: 1

| | | | | | |
|---|---|---|---|---|---|
| atgaagatca | tattctttt | atgttcattt | cttttttta | ttataaatac | acaatgtgta | 60 |
| acacatgaaa | gttatcaaga | acttgtcaaa | aaactagaag | ctttagaaga | tgcagtattg | 120 |
| acaggttata | gtttatttca | aaaggaaaaa | atggtattaa | atgaaggaac | aagtggaaca | 180 |
| gctgttacaa | ctagtacacc | tggttcaaag | ggttcagttg | cttcaggtgg | ttcaggtggc | 240 |
| tcagttgctt | caggtggctc | agttgcttca | ggtggctcag | ttgcttcagg | tggctcagtt | 300 |
| gcttcaggtg | gttcaggtaa | ttcaagacgt | acaaatcctt | cagataattc | aagtgattca | 360 |
| gatgctaaat | cttacgctga | tttaaaacac | agagtacgaa | attacttgtt | aactatcaaa | 420 |
| gaactcaaat | atcctcaact | ctttgattta | actaatcata | tgttaacttt | gtgtgataat | 480 |
| attcatggtt | tcaaatattt | aattgatgga | tatgaagaaa | ttaatgaatt | attatataaa | 540 |
| ttaaacttt | attttgattt | attaagagca | aaattaaatg | atgtatgtgc | taatgattat | 600 |
| tgtcaaatac | ctttcaatct | taaaattcgt | gcaaatgaat | tagacgtact | taaaaaactt | 660 |
| gtgttcggat | atagaaaacc | attagacaat | attaaagata | atgtaggaaa | aatggaagat | 720 |
| tacattaaaa | aaaataaaaa | aaccatagaa | aatataaatg | aattaattga | agaaagtaag | 780 |
| aaaacaattg | ataaaaataa | gaatgcaact | aagaagaag | aaaaaaaaaa | attataccaa | 840 |
| gctcaatatg | atctttctat | ttacaataaa | caattagaag | aagcacataa | tttaataagc | 900 |
| gttttagaaa | aacgtattga | cactttaaaa | aaaatgaaa | acattaagga | attacttgat | 960 |
| aagataaatg | aaattaaaaa | tcccccaccg | gccaattctg | gaaatacacc | aaatactctc | 1020 |
| cttgataaga | acaaaaaaat | cgaggaacac | gaaaagaaa | taaagaaat | tgccaaaact | 1080 |
| attaaattta | atattgatag | tttatttact | gatccacttg | aattagaata | ctatttaaga | 1140 |
| gaaaaaaata | aaaatattga | tataagtgca | aaggttgaaa | caaggaatc | aactgaaccc | 1200 |
| aatgaatatc | caaatggagt | tacttatcct | ttgtcatata | acgatattaa | caatgcttta | 1260 |
| aatgaactta | attcttttgg | tgatttaatt | aatccatttg | attatacaaa | agaaccaagt | 1320 |
| aaaacatat | atactgataa | tgaaagaaaa | aaattcataa | atgaaattaa | ggaaaaaatt | 1380 |
| aaaatagaaa | aaaaaaaaat | tgaatctgat | aaaaaatctt | acgaagacag | atctaagtct | 1440 |
| ttaaatgata | taacaaaaga | atatgaaaaa | ttacttaatg | aaatttatga | tagcaaattc | 1500 |
| aataataata | tagatttaac | taatttcgaa | aaaatgatgg | gtaaaagata | ttcatataaa | 1560 |
| gttgagaaac | ttcacacaca | taatactttt | gcatcctatg | aaaattctaa | acataatctt | 1620 |
| gaaaagttaa | caaagctct | aaatatatg | gaagattatt | ctttaaggaa | tatagtagtt | 1680 |
| gaaaagaat | taaatatta | taaaattta | ataagcaaaa | tagaaaatga | gattgaaaca | 1740 |
| ttagttgaaa | atattaaaaa | agatgaagaa | cagcttttg | aaaaaaaaat | tactaaagac | 1800 |
| gaaaatatac | cagatgaaaa | aatttagaa | gtatctgaca | ttgtaaaagt | acaagttcaa | 1860 |
| aaagttttat | taatgaacaa | aattgacgaa | ttaaaaaaga | ctcaattgat | tttaaaaat | 1920 |
| gtagaattaa | aacataatat | acatgttccc | aattcttaca | aacaagaaaa | taagcaagaa | 1980 |
| ccttattatt | taattgtgtt | gaaaaagaa | attgataaat | taaagtgtt | catgcctaag | 2040 |

-continued

```
gtagaatcat tgataaatga agaaaaaaaa aacataaaaa cagaaggtca atcggataat    2100
tcggaaccat caaccgaagg agaaataaca ggacaagcaa ctacaaaacc tggacaacaa    2160
gcaggatctg ctttagaagg agattcagta caagcacaag cacaagaaca aaaacaagca    2220
caaccaccag taccagtacc agtaccagaa gcaaaagcac aagtcccaac accaccagca    2280
ccagtaaata taaaaactga aaatgtttcc aaattagatt atcttgaaaa attatatgaa    2340
ttttaaaata cttcatatat atgtcacaaa tatattttgg tttcacactc aactatgaac    2400
gaaaagatat taaacaata taaaattaca aggaggaag aaagcaaatt aagttcatgt      2460
gatccattag acttattgtt taatatacaa ataacatac ctgtaatgta ttctatgttt     2520
gatagcttaa acaatagttt atcacaacta tttatggaaa tttatgaaaa agaaatggtt    2580
tgtaatttat ataaacttaa ggataatgac aaaattaaaa atttattaga ggaagcgaaa    2640
aaagtatcca catctgtaaa aactctttca agttcatcaa tgcaaccatt atcattaaca    2700
cctcaggata aacccgaagt aagtgcaaat gatgatacat cacattctac aaatttgaat    2760
aatagtttaa aattatttga aaacatattg agtcttggaa aaacaaaaa tatataccaa     2820 gaattaatag gtcaaaaaag tagtgaaaac ttttatgaaa agatattaaa agatagtgat    2880
acattttata atgaatcttt tacaaatttt gtaaaatcta aagctgatga tattaattca    2940
ttgaatgatg aatcaaaaag gaagaaatta gaagaagata ttaataaatt aaaaaaaact    3000
ttacagttat catttgattt atataataaa tataaaattaa aattagaaag attatttgat   3060
aaaaagaaaa cagttggtaa atataaaatg caaattaaaa aacttactttt attaaaagaa   3120 caattagaat caaaattgaa ttcacttaat aacccaaagc atgtattaca aaacttttct    3180
gttttcttta acaaaaaaaa agaagctgaa atagcagaaa ctgaaaacac attagaaaac    3240
acaaaaatat tattgaaaca ttataaagga cttgttaaat attataatgg tgaatcatct    3300
ccattaaaaa ctttaagtga agaatcaatt caaacagaag ataattatgc cagtttagaa    3360
aactttaaag tattaagtaa attagaagga aaattaaagg ataatttaaa tttagaaaag    3420
aaaaaattat catacttatc aagtggatta catcatttaa ttgctgaatt aaaagaagta    3480
ataaaaaata aaaattatac aggtaattct ccaagtgaaa ataatacgga tgttaacaat    3540
gcattagaat cttacaaaaa atttctccca gaaggaacag atgttgcaac agttgtaagt    3600
gaaagtggat ccgacacatt agaacaaagt caaccaaaga aaccagcatc aactcatgta    3660
ggagcagagt ctaacacaat aacaacatca caaaatgtcg atgatgaagt agatgacgta    3720
atcatagtac ctatatttgg agaatccgaa gaagattatg atgatttagg acaagtagta    3780
acaggagaag cagtaactcc ttccgtaatt gataacatac tttctaaaat tgaaaatgaa    3840
tatgaggttt tatatttaaa acctttagca ggtgtttata gaagtttaaa aaaacaatta    3900
gaaaataacg ttatgacatt taatgttaat gttaaggata tttttaaattc acgatttaat   3960 aaacgtgaaa atttcaaaaa tgttttagaa tcagatttaa ttccatataa agatttaaca    4020
tcaagtaatt atgttgtcaa agatccatat aaatttctta ataaagaaaa aagagataaa    4080
ttcttaagca gttataatta tattaaggat tcaatagata cggatataaa ttttgcaaat    4140
gatgttcttg gatattataa aatattatcc gaaaaatata atcgagattt agattcaatt    4200
aaaaaatata tcaacgacaa acaaggtgaa aatgagaaat accttcccctt tttaaacaat   4260 attgagacct tatataaaac agttaatgat aaaattgatt tatttgtaat tcattttagaa   4320 gcaaaagttc taaattatac atatgagaaa tcaaacgtag aagttaaaat aaaagaactt    4380
```

-continued

| | |
|---|---|
| aattacttaa aaacaattca agacaaattg gcagatttta aaaaaaataa caatttcgtt | 4440 |
| ggaattgctg atttatcaac agattataac cataataact tattgacaaa gttccttagt | 4500 |
| acaggtatgg tttttgaaaa tcttgctaaa accgttttat ctaatttact tgatggaaac | 4560 |
| ttgcaaggta tgttaaacat ttcacaacac caatgcgtaa aaaaacaatg tccacaaaat | 4620 |
| tctggatgtt tcagacattt agatgaaaga gaagaatgta aatgtttatt aaattacaaa | 4680 |
| caagaaggtg ataaatgtgt tgaaaatcca atcctactt gtaacgaaaa taatggtgga | 4740 |
| tgtgatgcag atgccaaatg taccgaagaa gattcaggta gcaacggaaa gaaaatcaca | 4800 |
| tgtgaatgta ctaaacctga ttcttatcca cttttcgatg gtatttctg cagttcctct | 4860 |
| aacttcttag gaatatcatt cttattaata ctcatgttaa tattatacag tttcatttaa | 4920 |

<210> SEQ ID NO 2
<211> LENGTH: 4940
<212> TYPE: DNA
<213> ORGANISM: Plasmodium falciparum

<400> SEQUENCE: 2

| | |
|---|---|
| cgcacgcgta tgaaaatcat tttcttcctc tgttcatttc tgttttttat catcaatact | 60 |
| cagtgcgtga cccacgaatc ctatcaggag ctggttaaga aactggaagc tttggaagat | 120 |
| gccgtcctta ccggatacag cctgttccag aaggagaaga tggtgctgaa tgaagggacg | 180 |
| agtggcacgg ccgttacaac cagcacaccc ggttctaaag ggtctgtggc tagcggtggc | 240 |
| tccggtgggt ctgtggcctc tgggggttcc gtcgcctccg gcggcagcgt ggcatcaggt | 300 |
| ggctcagtgg caagcggcgg ttccgggaac agtcgaagaa ccaatccatc tgacaactct | 360 |
| agcgattccg acgccaagtc ctacgccgac ctcaagcacc gagtgagaaa ctatctcctc | 420 |
| actatcaagg agctgaagta cccacagttg ttcgacctca ctaatcatat gctgacactg | 480 |
| tgtgataaca ttcatggctt caaatatctg attgacggtt acgaagagat caatgaactc | 540 |
| ctgtacaagt tgaatttcta cttcgacttg ctaagggcca aactgaatga cgtttgcgcc | 600 |
| aatgactatt gtcaaattcc attcaatttg aagatcagag ccaacgagtt ggacgtattg | 660 |
| aagaagttgg tcttcggata tcgcaagcct ctcgacaaca tcaaggacaa tgtgggaaag | 720 |
| atggaagatt atattaaaaa gaataagaag accatcgaga acattaacga gctgatcgaa | 780 |
| gaatccaaaa agaccataga caaaaataag aatgcaacca aggaggaaga aaagaagaag | 840 |
| ttgtaccagg cccagtacga cctgtccatc tataacaaac agcttgaaga agcccataac | 900 |
| ctcatcagcg tactggagaa gcgcatagac accctcaaga agaatgaaaa tatcaaagaa | 960 |
| ctgctcgaca agattaatga aattaagaat cctccgccag ccaactctgg gaacacccct | 1020 |
| aacacgctgc tggacaagaa caagaagata gaggagcacg agaaagagat caagagatc | 1080 |
| gccaaaacca ttaagttcaa catagattct ctctttactg atccccttga gctggagtac | 1140 |
| tacttgagag agaagaataa gaatatagac atctccgcca aagtcgagac aaaggaatca | 1200 |
| accgaaccta tgaatatcc caatggtgtg acgtaccctc tgtcttataa cgatatcaac | 1260 |
| aacgctctca cgagctcaa tagcttcggt gacttgatta cccccttcga ttatacgaaa | 1320 |
| gaaccctcta gaatatctca cacagacaat gagagaaaga gtttatcaa cgaaatcaag | 1380 |
| gagaagatca aaattgagaa gagaaaatt gagagtgaca agaaaagtta cgaagaccgc | 1440 |
| agcaaaagtc taaacgatat cactaaagag tatgaaaagc tgctgaacga gatctatgat | 1500 |
| tccaaattca caataacat cgacctgacc aacttcgaga aaatgatggg aaaacggtac | 1560 |
| tcttacaaag tggagaaact gacacaccat aataccttg catcctatga gaattctaag | 1620 |

-continued

```
cataatcttg agaagctcac caaagctctt aagtatatgg aggactattc tctgcggaac    1680
attgttgtgg agaaagaact aaagtattac aagaatctca taagtaagat cgaaaacgag    1740
atcgagacgc ttgttgagaa cattaagaag gatgaagaac agttgtttga agaagaagatt   1800 acaaaagacg aaaataaacc agatgagaag atcctggagg tctccgatat tgttaaagtc    1860
caagtgcaga aggtgctcct catgaacaag attgatgaac tcaagaagac tcaactcatt    1920
ctgaagaacg tggagttaaa acataatata catgtgccga atagttataa gcaggagaat    1980
aagcaggaac catactacct catcgtactc aagaaagaga tagacaaaact gaaagtgttc    2040 atgcccaaag tcgagagcct gatcaacgaa gagaagaaga acattaaaac tgaaggacag    2100
tcagataact ccgagccttc cacagaagga gagataaccg gacaggctac caccaagccc    2160
ggacaacagg ccggttcagc tctcgaaggc gatagcgtgc aagctcaagc acaagagcag    2220
aagcaggcac agcctccagt gccagtgccc gttccagagg ctaaagctca agtgcctaca    2280
ccaccagctc ctgtgaataa caagaccgag aatgtcagca aactggacta ccttgagaag    2340
ctctatgagt tcctgaatac atcctacatc tgccacaaat atatcctcgt ctctcacagc    2400
actatgaacg agaagattct taaacagtac aagataacca aggaagagga gagtaaactg    2460
tcctcttgtg atccactgga cctgctgttc aatatccaga acaacattcc cgttatgtat    2520
tctatgttcg atagcctcaa caattctctc tctcaactgt tcatggagat atatgagaag    2580
gagatggtct gcaacctgta taaactcaaa gacaacgaca agattaagaa ccttctggag    2640
gaagctaaga aggtctccac ctctgttaaa actctctctt ccagctccat gcaaccactg    2700
tctctcacac ctcaagacaa gcccgaagtg agcgctaacg acgacacctc tcactcgacc    2760
aaccttaata actcactgaa actgtttgag aacatcctgt ctctcggcaa gaataagaac    2820
atctaccaag aacttattgg acagaaatcg tccgagaact tctacgagaa gatactgaaa    2880
gacagcgaca cattctataa cgagagcttc actaacttcg tgaaatctaa agccgatgat    2940
atcaactctc ttaacgatga atctaaacgt aagaagctgg aagaggacat caataagctg    3000 aagaagcacac tgcaactgag cttcgacctg tacaacaagt acaaactgaa actggagaga    3060
ctcttcgaca agaagaagac agtcggcaag tataagatgc agatcaagaa gttgactctg    3120
ctcaaggagc agcttgaaag caaactcaac tcactgaaca atccgaaaca cgtactgcag    3180
aacttctcag tgttcttcaa caagaagaag aagccgaga tcgccgagac agagaacact    3240
ctggagaaca ccaagattct tctcaaacac tacaaaggcc tcgtcaagta ttataatggc    3300
gagtcttctc ctctgaagac tctctccgag gagagcatcc agaccgagga taactacgcc    3360
agcctcgaga acttcaaggt cctgtctaag ctcgaaggca gctgaagga caacctgaac    3420 ctggagaaga agaagctcag ctacctctct agcggactgc atcacctgat cgccgagctc    3480
aaggaagtca ttaagaacaa gaactacacc ggcaatagcc caagcgagaa taatacagac    3540
gtgaataacg cactggaatc ttacaagaag ttcctgcctg aaggaacaga tgtcgccact    3600
gtggtgtctg aatctggctc cgacacactg gagcagtctc aacctaagaa gcctgcatct    3660
actcatgtcg gagccgagtc caatacaatt accacatctc agaacgtcga cgatgaggtc    3720
gatgacgtca tcattgtgcc tatcttcggc gagagcgagg aggactacga tgacctcggc    3780
caggtggtca ccggtgaggc tgtcactcct tccgtgattg ataacattct gtccaaaatc    3840
gagaacgaat acgaagtgct ctatctgaaa cctctggcag gcgtctatag gtctctcaag    3900
aaacagctgg agaataacgt gatgaccttc aatgtcaacg tgaaggacat tctgaacagc    3960
```

-continued

```
cgctttaata agagagaaaa tttcaagaac gtcttggaga gcgacttgat tccctataaa   4020
gacctgacct cctctaacta cgttgtcaag gacccataca agttcctcaa taaagagaag   4080
agggataaat ttctgtctag ttacaactat atcaaggact ccatcgacac cgatatcaat   4140
ttcgctaatg atgtgctggg gtattacaag atcctgagcg aaaaatacaa gtctgacctt   4200
gactctatta aaagtatat caacgataag caaggcgaga atgaaaaata tctgcccttc   4260
ctgaataaca tcgaaaccct gtacaagaca gtgaacgaca aaatcgacct cttcgtaatt   4320
cacctggagg ccaaggtcct caactatact tacgagaaga gcaatgtgga agttaaaatc   4380
aaggagctga actacctcaa aacaatccaa gacaagctgg cagatttcaa gaaaaataac   4440
aatttcgtcg gaattgcaga cctgtctacc gattataacc acaacaatct cctgaccaag   4500
tttctgtcca ctggcatggt gttcgaaaac ctcgccaaaa cagtgctgag caatctgctc   4560
gacggcaacc tgcagggcat gctgaacatc tcccagcacc aatgcgtgaa gaaacagtgc   4620
ccccagaata gcggctgttt caggcatctg gacgagcgcg aagagtgcaa gtgtctcctg   4680
aactacaaac aagaaggaga taagtgcgtg gagaacccaa accctacctg caatgaaaac   4740
aatggcgggt gtgacgccga tgctaaatgc accgaggaag acagcggctc taacggaaag   4800
aaaatcacat gcgagtgtac taagcccgac tcctatccac tcttcgacgg gatttttttgc   4860
tccagctcta atttcctggg catctccttc ctgctgatcc tcatgctgat cctgtacagc   4920
ttcatctaat agatcgatgg                                               4940
```

<210> SEQ ID NO 3
<211> LENGTH: 1639
<212> TYPE: PRT
<213> ORGANISM: Plasmodium falciparum

<400> SEQUENCE: 3

```
Met Lys Ile Ile Phe Phe Leu Cys Ser Phe Leu Phe Phe Ile Ile Asn
 1               5                  10                  15

Thr Gln Cys Val Thr His Glu Ser Tyr Gln Glu Leu Val Lys Lys Leu
            20                  25                  30

Glu Ala Leu Glu Asp Ala Val Leu Thr Gly Tyr Ser Leu Phe Gln Lys
        35                  40                  45

Glu Lys Met Val Leu Asn Glu Gly Thr Ser Gly Thr Ala Val Thr Thr
    50                  55                  60

Ser Thr Pro Gly Ser Lys Gly Ser Val Ala Ser Gly Ser Gly Gly
65                  70                  75                  80

Ser Val Ala Ser Gly Gly Ser Val Ala Ser Gly Gly Ser Val Ala Ser
                85                  90                  95

Gly Gly Ser Val Ala Ser Gly Gly Ser Gly Asn Ser Arg Arg Thr Asn
            100                 105                 110

Pro Ser Asp Asn Ser Ser Asp Ser Asp Ala Lys Ser Tyr Ala Asp Leu
        115                 120                 125

Lys His Arg Val Arg Asn Tyr Leu Leu Thr Ile Lys Glu Leu Lys Tyr
    130                 135                 140

Pro Gln Leu Phe Asp Leu Thr Asn His Met Leu Thr Leu Cys Asp Asn
145                 150                 155                 160

Ile His Gly Phe Lys Tyr Leu Ile Asp Gly Tyr Glu Glu Ile Asn Glu
                165                 170                 175

Leu Leu Tyr Lys Leu Asn Phe Tyr Phe Asp Leu Leu Arg Ala Lys Leu
            180                 185                 190

Asn Asp Val Cys Ala Asn Asp Tyr Cys Gln Ile Pro Phe Asn Leu Lys
```

-continued

```
            195                 200                 205
Ile Arg Ala Asn Glu Leu Asp Val Leu Lys Lys Leu Val Phe Gly Tyr
    210                 215                 220

Arg Lys Pro Leu Asp Asn Ile Lys Asp Asn Val Gly Lys Met Glu Asp
225                 230                 235                 240

Tyr Ile Lys Lys Asn Lys Lys Thr Ile Glu Asn Ile Asn Glu Leu Ile
                245                 250                 255

Glu Glu Ser Lys Lys Thr Ile Asp Lys Asn Lys Asn Ala Thr Lys Glu
                260                 265                 270

Glu Glu Lys Lys Lys Leu Tyr Gln Ala Gln Tyr Asp Leu Ser Ile Tyr
            275                 280                 285

Asn Lys Gln Leu Glu Glu Ala His Asn Leu Ile Ser Val Leu Glu Lys
    290                 295                 300

Arg Ile Asp Thr Leu Lys Lys Asn Glu Asn Ile Lys Glu Leu Leu Asp
305                 310                 315                 320

Lys Ile Asn Glu Ile Lys Asn Pro Pro Ala Asn Ser Gly Asn Thr
                325                 330                 335

Pro Asn Thr Leu Leu Asp Lys Asn Lys Lys Ile Glu Glu His Glu Lys
                340                 345                 350

Glu Ile Lys Glu Ile Ala Lys Thr Ile Lys Phe Asn Ile Asp Ser Leu
            355                 360                 365

Phe Thr Asp Pro Leu Glu Leu Glu Tyr Tyr Leu Arg Glu Lys Asn Lys
    370                 375                 380

Asn Ile Asp Ile Ser Ala Lys Val Glu Thr Lys Glu Ser Thr Glu Pro
385                 390                 395                 400

Asn Glu Tyr Pro Asn Gly Val Thr Tyr Pro Leu Ser Tyr Asn Asp Ile
                405                 410                 415

Asn Asn Ala Leu Asn Glu Leu Asn Ser Phe Gly Asp Leu Ile Asn Pro
                420                 425                 430

Phe Asp Tyr Thr Lys Glu Pro Ser Lys Asn Ile Tyr Thr Asp Asn Glu
            435                 440                 445

Arg Lys Lys Phe Ile Asn Glu Ile Lys Glu Lys Ile Lys Ile Glu Lys
    450                 455                 460

Lys Lys Ile Glu Ser Asp Lys Lys Ser Tyr Glu Asp Arg Ser Lys Ser
465                 470                 475                 480

Leu Asn Asp Ile Thr Lys Glu Tyr Glu Lys Leu Leu Asn Glu Ile Tyr
                485                 490                 495

Asp Ser Lys Phe Asn Asn Asn Ile Asp Leu Thr Asn Phe Glu Lys Met
                500                 505                 510

Met Gly Lys Arg Tyr Ser Tyr Lys Val Glu Lys Leu Thr His His Asn
            515                 520                 525

Thr Phe Ala Ser Tyr Glu Asn Ser Lys His Asn Leu Glu Lys Leu Thr
    530                 535                 540

Lys Ala Leu Lys Tyr Met Glu Asp Tyr Ser Leu Arg Asn Ile Val Val
545                 550                 555                 560

Glu Lys Glu Leu Lys Tyr Tyr Lys Asn Leu Ile Ser Lys Ile Glu Asn
                565                 570                 575

Glu Ile Glu Thr Leu Val Glu Asn Ile Lys Lys Asp Glu Glu Gln Leu
                580                 585                 590

Phe Glu Lys Lys Ile Thr Lys Asp Glu Asn Lys Pro Asp Glu Lys Ile
            595                 600                 605

Leu Glu Val Ser Asp Ile Val Lys Val Gln Val Gln Lys Val Leu Leu
    610                 615                 620
```

-continued

```
Met Asn Lys Ile Asp Glu Leu Lys Lys Thr Gln Leu Ile Leu Lys Asn
625                 630                 635                 640

Val Glu Leu Lys His Asn Ile His Val Pro Asn Ser Tyr Lys Gln Glu
            645                 650                 655

Asn Lys Gln Glu Pro Tyr Tyr Leu Ile Val Leu Lys Lys Glu Ile Asp
        660                 665                 670

Lys Leu Lys Val Phe Met Pro Lys Val Glu Ser Leu Ile Asn Glu Glu
            675                 680                 685

Lys Lys Asn Ile Lys Thr Glu Gly Gln Ser Asp Asn Ser Glu Pro Ser
        690                 695                 700

Thr Glu Gly Glu Ile Thr Gly Gln Ala Thr Thr Lys Pro Gly Gln Gln
705                 710                 715                 720

Ala Gly Ser Ala Leu Glu Gly Asp Ser Val Gln Ala Gln Ala Gln Glu
            725                 730                 735

Gln Lys Gln Ala Gln Pro Pro Val Pro Val Pro Val Pro Glu Ala Lys
        740                 745                 750

Ala Gln Val Pro Thr Pro Pro Ala Pro Val Asn Asn Lys Thr Glu Asn
            755                 760                 765

Val Ser Lys Leu Asp Tyr Leu Glu Lys Leu Tyr Glu Phe Leu Asn Thr
770                 775                 780

Ser Tyr Ile Cys His Lys Tyr Ile Leu Val Ser His Ser Thr Met Asn
785                 790                 795                 800

Glu Lys Ile Leu Lys Gln Tyr Lys Ile Thr Lys Glu Glu Ser Lys
            805                 810                 815

Leu Ser Ser Cys Asp Pro Leu Asp Leu Leu Phe Asn Ile Gln Asn Asn
            820                 825                 830

Ile Pro Val Met Tyr Ser Met Phe Asp Ser Leu Asn Asn Ser Leu Ser
            835                 840                 845

Gln Leu Phe Met Glu Ile Tyr Glu Lys Glu Met Val Cys Asn Leu Tyr
850                 855                 860

Lys Leu Lys Asp Asn Asp Lys Ile Lys Asn Leu Leu Glu Glu Ala Lys
865                 870                 875                 880

Lys Val Ser Thr Ser Val Lys Thr Leu Ser Ser Ser Met Gln Pro
            885                 890                 895

Leu Ser Leu Thr Pro Gln Asp Lys Pro Glu Val Ser Ala Asn Asp Asp
            900                 905                 910

Thr Ser His Ser Thr Asn Leu Asn Asn Ser Leu Lys Leu Phe Glu Asn
        915                 920                 925

Ile Leu Ser Leu Gly Lys Asn Lys Asn Ile Tyr Gln Glu Leu Ile Gly
        930                 935                 940

Gln Lys Ser Ser Glu Asn Phe Tyr Glu Lys Ile Leu Lys Asp Ser Asp
945                 950                 955                 960

Thr Phe Tyr Asn Glu Ser Phe Thr Asn Phe Val Lys Ser Lys Ala Asp
            965                 970                 975

Asp Ile Asn Ser Leu Asn Asp Glu Ser Lys Arg Lys Lys Leu Glu Glu
            980                 985                 990

Asp Ile Asn Lys Leu Lys Lys Thr Leu Gln Leu Ser Phe Asp Leu Tyr
        995                 1000                1005

Asn Lys Tyr Lys Leu Lys Leu Glu Arg Leu Phe Asp Lys Lys Lys Thr
        1010                1015                1020

Val Gly Lys Tyr Lys Met Gln Ile Lys Lys Leu Thr Leu Leu Lys Glu
1025                1030                1035                1040
```

-continued

```
Gln Leu Glu Ser Lys Leu Asn Ser Leu Asn Asn Pro Lys His Val Leu
            1045                1050                1055

Gln Asn Phe Ser Val Phe Asn Lys Lys Lys Glu Ala Glu Ile Ala
            1060                1065                1070

Glu Thr Glu Asn Thr Leu Glu Asn Thr Lys Ile Leu Leu Lys His Tyr
        1075                1080                1085

Lys Gly Leu Val Lys Tyr Tyr Asn Gly Glu Ser Ser Pro Leu Lys Thr
    1090                1095                1100

Leu Ser Glu Glu Ser Ile Gln Thr Glu Asp Asn Tyr Ala Ser Leu Glu
1105                1110                1115                1120

Asn Phe Lys Val Leu Ser Lys Leu Glu Gly Lys Leu Lys Asp Asn Leu
                1125                1130                1135

Asn Leu Glu Lys Lys Lys Leu Ser Tyr Leu Ser Ser Gly Leu His His
                1140                1145                1150

Leu Ile Ala Glu Leu Lys Glu Val Ile Lys Asn Lys Asn Tyr Thr Gly
            1155                1160                1165

Asn Ser Pro Ser Glu Asn Asn Thr Asp Val Asn Asn Ala Leu Glu Ser
        1170                1175                1180

Tyr Lys Lys Phe Leu Pro Glu Gly Thr Asp Val Ala Thr Val Val Ser
1185                1190                1195                1200

Glu Ser Gly Ser Asp Thr Leu Glu Gln Ser Gln Pro Lys Lys Pro Ala
            1205                1210                1215

Ser Thr His Val Gly Ala Glu Ser Asn Thr Ile Thr Thr Ser Gln Asn
            1220                1225                1230

Val Asp Asp Glu Val Asp Val Ile Ile Val Pro Ile Phe Gly Glu
        1235                1240                1245

Ser Glu Glu Asp Tyr Asp Asp Leu Gly Gln Val Val Thr Gly Glu Ala
        1250                1255                1260

Val Thr Pro Ser Val Ile Asp Asn Ile Leu Ser Lys Ile Glu Asn Glu
1265                1270                1275                1280

Tyr Glu Val Leu Tyr Leu Lys Pro Leu Ala Gly Val Tyr Arg Ser Leu
            1285                1290                1295

Lys Lys Gln Leu Glu Asn Asn Val Met Thr Phe Asn Val Asn Val Lys
            1300                1305                1310

Asp Ile Leu Asn Ser Arg Phe Asn Lys Arg Glu Asn Phe Lys Asn Val
            1315                1320                1325

Leu Glu Ser Asp Leu Ile Pro Tyr Lys Asp Leu Thr Ser Ser Asn Tyr
        1330                1335                1340

Val Val Lys Asp Pro Tyr Lys Phe Leu Asn Lys Glu Lys Arg Asp Lys
1345                1350                1355                1360

Phe Leu Ser Ser Tyr Asn Tyr Ile Lys Asp Ser Ile Asp Thr Asp Ile
            1365                1370                1375

Asn Phe Ala Asn Asp Val Leu Gly Tyr Tyr Lys Ile Leu Ser Glu Lys
            1380                1385                1390

Tyr Lys Ser Asp Leu Asp Ser Ile Lys Lys Tyr Ile Asn Asp Lys Gln
        1395                1400                1405

Gly Glu Asn Glu Lys Tyr Leu Pro Phe Leu Asn Asn Ile Glu Thr Leu
    1410                1415                1420

Tyr Lys Thr Val Asn Asp Lys Ile Asp Leu Phe Val Ile His Leu Glu
1425                1430                1435                1440

Ala Lys Val Leu Asn Tyr Thr Tyr Glu Lys Ser Asn Val Glu Val Lys
                1445                1450                1455

Ile Lys Glu Leu Asn Tyr Leu Lys Thr Ile Gln Asp Lys Leu Ala Asp
```

-continued

```
                1460              1465              1470
Phe Lys Lys Asn Asn Asn Phe Val Gly Ile Ala Asp Leu Ser Thr Asp
        1475              1480              1485
Tyr Asn His Asn Asn Leu Leu Thr Lys Phe Leu Ser Thr Gly Met Val
    1490              1495              1500
Phe Glu Asn Leu Ala Lys Thr Val Leu Ser Asn Leu Leu Asp Gly Asn
1505              1510              1515              1520
Leu Gln Gly Met Leu Asn Ile Ser Gln His Gln Cys Val Lys Lys Gln
            1525              1530              1535
Cys Pro Gln Asn Ser Gly Cys Phe Arg His Leu Asp Glu Arg Glu Glu
        1540              1545              1550
Cys Lys Cys Leu Leu Asn Tyr Lys Gln Glu Gly Asp Lys Cys Val Glu
        1555              1560              1565
Asn Pro Asn Pro Thr Cys Asn Glu Asn Asn Gly Gly Cys Asp Ala Asp
        1570              1575              1580
Ala Lys Cys Thr Glu Glu Asp Ser Gly Ser Asn Gly Lys Lys Ile Thr
1585              1590              1595              1600
Cys Glu Cys Thr Lys Pro Asp Ser Tyr Pro Leu Phe Asp Gly Ile Phe
            1605              1610              1615
Cys Ser Ser Ser Asn Phe Leu Gly Ile Ser Phe Leu Leu Ile Leu Met
            1620              1625              1630
Leu Ile Leu Tyr Ser Phe Ile
        1635
```

<210> SEQ ID NO 4
<211> LENGTH: 4894
<212> TYPE: DNA
<213> ORGANISM: Plasmodium falciparum

<400> SEQUENCE: 4

```
gcacgcgtat gaaaatcatt ttcttcctct gttcatttct gtttttatc atcaatactc      60
agtgcgtgac ccacgaatcc tatcaggagc tggttaagaa actggaagct ttggaagatg    120
ccgtccttac cggatacagc ctgttccaga aggagaagat ggtgctgaat gaagggacga    180
gtggcacggc cgttacaacc agcacacccg ttctaaagg gtctgtggct agcggtggct    240
ccggtgggtc tgtggcctct gggggttccg tcgcctccgg cggcagcgtg gcatcaggtg    300
gctcagtggc aagcggcggt tccgggaaca gtcgaagaac caatccatct gacaactcta    360
gcgattccga cgccaagtcc tacgccgacc tcaagcaccg agtgagaaac tatctcctca    420
ctatcaagga gctgaagtac ccacagttgt tcgacctcac taatcatatg ctgacactgt    480
gtgataacat tcatggcttc aaatatctga ttgacggtta cgaagagatc aatgaactcc    540
tgtacaagtt gaatttctac ttcgacttgc taagggccaa actgaatgac gtttgcgcca    600
atgactattg tcaaattcca ttcaatttga agatcgagc caacgagttg gacgtattga    660
agaagttggt cttcggatat cgcaagcctc tcgacaacat caaggacaat gtgggaaaga    720
tggaagatta tattaaaaag aataagaaga ccatcgagaa cattaacgag ctgatcgaag    780
aatccaaaaa gaccatagac aaaaataaga atgcaaccaa ggaggaagaa aagaagaagt    840
tgtaccaggc ccagtacgac ctgtccatct ataacaaaca gcttgaagaa gcccataacc    900
tcatcagcgt actggagaag cgcatagaca ccctcaagaa gaatgaaaat atcaaagaac    960
tgctcgacaa gattaatgaa attaagaatc ctccgccagc caactctggg aacacccta   1020
acacgctgct ggacaagaac aagaagatag aggagcacga gaaagagatc aagagatcg   1080
```

```
ccaaaaccat taagttcaac atagattctc tctttactga tccccttgag ctggagtact    1140
acttgagaga gaagaataag aatatagaca tctccgccaa agtcgagaca aaggaatcaa    1200
ccgaacctaa tgaatatccc aatggtgtga cgtaccctct gtcttataac gatatcaaca    1260
acgctctcaa cgagctcaat agcttcggtg acttgattaa ccccttcgat tatacgaaag    1320
aaccctctaa gaatatctac acagacaatg agagaaagaa gtttatcaac gaaatcaagg    1380
agaagatcaa aattgagaag aagaaaattg agagtgacaa gaaaagttac gaagaccgca    1440
gcaaaagtct aaacgatatc actaaagagt atgaaaagct gctgaacgag atctatgatt    1500
ccaaattcaa caataacatc gacctgacca acttcgagaa aatgatggga aaacggtact    1560
cttacaaagt ggagaaactg acacaccata atacctttgc atcctatgag aattctaagc    1620
ataatcttga gaagctcacc aaagctctta agtatatgga ggactattct ctgcggaaca    1680
ttgttgtgga gaaagaacta agtattaca agaatctcat aagtaagatc gaaaacgaga    1740
tcgagacgct tgttgagaac attaagaagg atgaagaaca gttgtttgag aagaagatta    1800
caaaagacga aaataaacca gatgagaaga tcctggaggt ctccgatatt gttaaagtcc    1860
aagtgcagaa ggtgctcctc atgaacaaga ttgatgaact caagaagact caactcattc    1920
tgaagaacgt ggagttaaaa cataatatac atgtgccgaa tagttataag caggagaata    1980
agcaggaacc atactacctc atcgtactca agaaagagat agacaaactg aaagtgttca    2040
tgcccaaagt cgagagcctg atcaacgaag agaagaagaa cattaaaact gaaggacagt    2100
cagataactc cgagccttcc acagaaggag agataaccgg acaggctacc accaagcccg    2160
gacaacaggc cggttcagct ctcgaaggcg atagcgtgca agctcaagca caagagcaga    2220
agcaggcaca gcctccagtg ccagtgcccg ttccagaggc taaagctcaa gtgcctacac    2280
caccagctcc tgtgaataac aagaccgaga atgtcagcaa actggactac cttgagaagc    2340
tctatgagtt cctgaataca tcctacatct gccacaaata tatcctcgtc tctcacagca    2400
ctatgaacga gaagattctt aaacagtaca agataaccaa ggaagaggag agtaaactgt    2460
cctcttgtga tccactggac ctgctgttca atatccagaa caacattccc gttatgtatt    2520
ctatgttcga tagcctcaac aattctctct ctcaactgtt catggagata tatgagaagg    2580
agatggtctg caacctgtat aaactcaaag acaacgacaa gattaagaac cttctggagg    2640
aagctaagaa ggtctccacc tctgttaaaa ctctctcttc cagctccatg caaccactgt    2700
ctctcacacc tcaagacaag cccgaagtga gcgctaacga cgacacctct cactcgacca    2760
accttaataa ctcactgaaa ctgtttgaga acatcctgtc tctcggcaag aataagaaca    2820
tctaccaaga acttattgga cagaaatcgt ccgagaactt ctacgagaag atactgaaag    2880
acagcgacac attctataac gagagcttca ctaacttcgt gaaatctaaa gccgatgata    2940
tcaactctct taacgatgaa tctaaacgta agaagctgga agaggacatc aataagctga    3000
agaagacact gcaactgagc ttcgacctgt acaacaagta caaactgaaa ctggagagac    3060
tcttcgacaa gaagaagaca gtcggcaagt ataagatgca gatcaagaag ttgactctgc    3120
tcaaggagca gcttgaaagc aaactcaact cactgaacaa tccgaaacac gtactgcaga    3180
acttctcagt gttcttcaac aagaagaagg aagccgagat cgccgagaca gagaacactc    3240
tggaaacac caagattctt ctcaaacact acaaaggcct cgtcaagtat tataatggcg    3300
agtcttctcc tctgaagact ctctccgagg agcatccca gaccgaggat aactacgcca    3360
gcctcgaaga cttcaaggtc ctgtctaagc tcgaaggcaa gctgaaggac aacctgaacc    3420
tggagaagaa gaagctcagc tacctctcta gcggactgca tcacctgatc gccgagctca    3480
```

```
aggaagtcat taagaacaag aactacaccg gcaatagccc aagcgagaat aatacagacg    3540
tgaataacgc actggaatct tacaagaagt tcctgcctga aggaacagat gtcgccactg    3600
tggtgtctga atctggctcc gacacactgg agcagtctca acctaagaag cctgcatcta    3660
ctcatgtcgg agccgagtcc aatacaatta ccacatctca gaacgtcgac gatgaggtcg    3720
atgacgtcat cattgtgcct atcttcggcg agagcgagga ggactacgat gacctcggcc    3780
aggtggtcac cggtgaggct gtcactcctt ccgtgattga taacattctg tccaaaatcg    3840
agaacgaata cgaagtgctc tatctgaaac ctctggcagg cgtctatagg tctctcaaga    3900
aacagctgga gaataacgtg atgaccttca atgtcaacgt gaaggacatt ctgaacagcc    3960
gctttaataa gagagaaaat ttcaagaacg tcttggagag cgacttgatt ccctataaag    4020
acctgacctc ctctaactac gttgtcaagg acccatacaa gttcctcaat aaagagaaga    4080
gggataaatt tctgtctagt tacaactata tcaaggactc catcgacacc gatatcaatt    4140
tcgctaatga tgtgctgggg tattacaaga tcctgagcga aaaatacaag tctgaccttg    4200
actctattaa aaagtatatc aacgataagc aaggcgagaa tgaaaaatat ctgcccttcc    4260
tgaataacat cgaaaccctg tacaagacag tgaacgacaa aatcgacctc ttcgtaattc    4320
acctggaggc caaggtcctc aactatactt acgagaagag caatgtggaa gttaaaatca    4380
aggagctgaa ctacctcaaa acaatccaag acaagctggc agatttcaag aaaaataaca    4440
atttcgtcgg aattgcagac ctgtctaccg attataacca caacaatctc ctgaccaagt    4500
ttctgtccac tggcatggtg ttcgaaaacc tcgccaaaac agtgctgagc aatctgctcg    4560
acggcaacct gcagggcatg ctgaacatct cccagcacca atgcgtgaag aaacagtgcc    4620
cccagaatag cggctgtttc aggcatctgg acgagcgcga agagtgcaag tgtctcctga    4680
actacaaaca agaaggagat aagtgcgtgg agaacccaaa ccctacctgc aatgaaaaca    4740
atggcgggtg tgacgccgat gctaaatgca ccgaggaaga cagcggctct aacgaaagag    4800
aaatcacatg cgagtgtact aagcccgact cctatccact cttcgacggg atttttgct    4860
ccagctctaa ttaataggcg gccgcatcga tggc                               4894
```

<210> SEQ ID NO 5
<211> LENGTH: 1621
<212> TYPE: PRT
<213> ORGANISM: Plasmodium falciparum

<400> SEQUENCE: 5

```
Met Lys Ile Ile Phe Phe Leu Cys Ser Phe Leu Phe Phe Ile Ile Asn
 1               5                  10                  15

Thr Gln Cys Val Thr His Glu Ser Tyr Gln Glu Leu Val Lys Lys Leu
            20                  25                  30

Glu Ala Leu Glu Asp Ala Val Leu Thr Gly Tyr Ser Leu Phe Gln Lys
        35                  40                  45

Glu Lys Met Val Leu Asn Glu Gly Thr Ser Gly Thr Ala Val Thr Thr
    50                  55                  60

Ser Thr Pro Gly Ser Lys Gly Ser Val Ala Ser Gly Ser Gly Gly
65                  70                  75                  80

Ser Val Ala Ser Gly Gly Ser Val Ala Ser Gly Gly Ser Val Ala Ser
                85                  90                  95

Gly Gly Ser Val Ala Ser Gly Gly Ser Gly Asn Ser Arg Arg Thr Asn
            100                 105                 110

Pro Ser Asp Asn Ser Ser Asp Ser Asp Ala Lys Ser Tyr Ala Asp Leu
```

-continued

```
               115                 120                 125
Lys His Arg Val Arg Asn Tyr Leu Leu Thr Ile Lys Glu Leu Lys Tyr
            130                 135                 140

Pro Gln Leu Phe Asp Leu Thr Asn His Met Leu Thr Leu Cys Asp Asn
145                 150                 155                 160

Ile His Gly Phe Lys Tyr Leu Ile Asp Gly Tyr Glu Ile Asn Glu
                165                 170                 175

Leu Leu Tyr Lys Leu Asn Phe Tyr Phe Asp Leu Leu Arg Ala Lys Leu
                180                 185                 190

Asn Asp Val Cys Ala Asn Asp Tyr Cys Gln Ile Pro Phe Asn Leu Lys
                195                 200                 205

Ile Arg Ala Asn Glu Leu Asp Val Leu Lys Lys Leu Val Phe Gly Tyr
            210                 215                 220

Arg Lys Pro Leu Asp Asn Ile Lys Asp Asn Val Gly Lys Met Glu Asp
225                 230                 235                 240

Tyr Ile Lys Lys Asn Lys Lys Thr Ile Glu Asn Ile Asn Glu Leu Ile
                245                 250                 255

Glu Glu Ser Lys Lys Thr Ile Asp Lys Asn Lys Asn Ala Thr Lys Glu
            260                 265                 270

Glu Glu Lys Lys Lys Leu Tyr Gln Ala Gln Tyr Asp Leu Ser Ile Tyr
            275                 280                 285

Asn Lys Gln Leu Glu Glu Ala His Asn Leu Ile Ser Val Leu Glu Lys
            290                 295                 300

Arg Ile Asp Thr Leu Lys Lys Asn Glu Asn Ile Lys Glu Leu Leu Asp
305                 310                 315                 320

Lys Ile Asn Glu Ile Lys Asn Pro Pro Ala Asn Ser Gly Asn Thr
                325                 330                 335

Pro Asn Thr Leu Leu Asp Lys Asn Lys Lys Ile Glu Glu His Glu Lys
                340                 345                 350

Glu Ile Lys Glu Ile Ala Lys Thr Ile Lys Phe Asn Ile Asp Ser Leu
            355                 360                 365

Phe Thr Asp Pro Leu Glu Leu Glu Tyr Tyr Leu Arg Glu Lys Asn Lys
370                 375                 380

Asn Ile Asp Ile Ser Ala Lys Val Glu Thr Lys Glu Ser Thr Glu Pro
385                 390                 395                 400

Asn Glu Tyr Pro Asn Gly Val Thr Tyr Pro Leu Ser Tyr Asn Asp Ile
                405                 410                 415

Asn Asn Ala Leu Asn Glu Leu Asn Ser Phe Gly Asp Leu Ile Asn Pro
            420                 425                 430

Phe Asp Tyr Thr Lys Glu Pro Ser Lys Asn Ile Tyr Thr Asp Asn Glu
            435                 440                 445

Arg Lys Lys Phe Ile Asn Glu Ile Lys Glu Lys Ile Lys Ile Glu Lys
450                 455                 460

Lys Lys Ile Glu Ser Asp Lys Lys Ser Tyr Glu Asp Arg Ser Lys Ser
465                 470                 475                 480

Leu Asn Asp Ile Thr Lys Glu Tyr Glu Lys Leu Leu Asn Glu Ile Tyr
                485                 490                 495

Asp Ser Lys Phe Asn Asn Asn Ile Asp Leu Thr Asn Phe Glu Lys Met
                500                 505                 510

Met Gly Lys Arg Tyr Ser Tyr Lys Val Glu Lys Leu Thr His His Asn
            515                 520                 525

Thr Phe Ala Ser Tyr Glu Asn Ser Lys His Asn Leu Glu Lys Leu Thr
            530                 535                 540
```

-continued

```
Lys Ala Leu Lys Tyr Met Glu Asp Tyr Ser Leu Arg Asn Ile Val Val
545                 550                 555                 560

Glu Lys Glu Leu Lys Tyr Tyr Lys Asn Leu Ile Ser Lys Ile Glu Asn
                565                 570                 575

Glu Ile Glu Thr Leu Val Glu Asn Ile Lys Lys Asp Glu Glu Gln Leu
            580                 585                 590

Phe Glu Lys Lys Ile Thr Lys Asp Glu Asn Lys Pro Asp Glu Lys Ile
        595                 600                 605

Leu Glu Val Ser Asp Ile Val Lys Val Gln Val Gln Lys Val Leu Leu
    610                 615                 620

Met Asn Lys Ile Asp Glu Leu Lys Lys Thr Gln Leu Ile Leu Lys Asn
625                 630                 635                 640

Val Glu Leu Lys His Asn Ile His Val Pro Asn Ser Tyr Lys Gln Glu
                645                 650                 655

Asn Lys Gln Glu Pro Tyr Tyr Leu Ile Val Leu Lys Lys Glu Ile Asp
                660                 665                 670

Lys Leu Lys Val Phe Met Pro Lys Val Glu Ser Leu Ile Asn Glu Glu
        675                 680                 685

Lys Lys Asn Ile Lys Thr Glu Gly Gln Ser Asp Asn Ser Glu Pro Ser
690                 695                 700

Thr Glu Gly Glu Ile Thr Gly Gln Ala Thr Thr Lys Pro Gly Gln Gln
705                 710                 715                 720

Ala Gly Ser Ala Leu Glu Gly Asp Ser Val Gln Ala Gln Ala Gln Glu
                725                 730                 735

Gln Lys Gln Ala Gln Pro Val Pro Val Pro Val Pro Glu Ala Lys
            740                 745                 750

Ala Gln Val Pro Thr Pro Pro Ala Pro Val Asn Asn Lys Thr Glu Asn
        755                 760                 765

Val Ser Lys Leu Asp Tyr Leu Glu Lys Leu Tyr Glu Phe Leu Asn Thr
    770                 775                 780

Ser Tyr Ile Cys His Lys Tyr Ile Leu Val Ser His Ser Thr Met Asn
785                 790                 795                 800

Glu Lys Ile Leu Lys Gln Tyr Lys Ile Thr Lys Glu Glu Ser Lys
                805                 810                 815

Leu Ser Ser Cys Asp Pro Leu Asp Leu Leu Phe Asn Ile Gln Asn Asn
                820                 825                 830

Ile Pro Val Met Tyr Ser Met Phe Asp Ser Leu Asn Asn Ser Leu Ser
        835                 840                 845

Gln Leu Phe Met Glu Ile Tyr Glu Lys Glu Met Val Cys Asn Leu Tyr
850                 855                 860

Lys Leu Lys Asp Asn Asp Lys Ile Lys Asn Leu Leu Glu Glu Ala Lys
865                 870                 875                 880

Lys Val Ser Thr Ser Val Lys Thr Leu Ser Ser Ser Ser Met Gln Pro
                885                 890                 895

Leu Ser Leu Thr Pro Gln Asp Lys Pro Glu Val Ser Ala Asn Asp Asp
            900                 905                 910

Thr Ser His Ser Thr Asn Leu Asn Asn Ser Leu Lys Leu Phe Glu Asn
        915                 920                 925

Ile Leu Ser Leu Gly Lys Asn Lys Asn Ile Tyr Gln Glu Leu Ile Gly
    930                 935                 940

Gln Lys Ser Ser Glu Asn Phe Tyr Glu Lys Ile Leu Lys Asp Ser Asp
945                 950                 955                 960
```

-continued

Thr Phe Tyr Asn Glu Ser Phe Thr Asn Phe Val Lys Ser Lys Ala Asp
                965                 970                 975

Asp Ile Asn Ser Leu Asn Asp Glu Ser Lys Arg Lys Lys Leu Glu Glu
            980                 985                 990

Asp Ile Asn Lys Leu Lys Lys Thr Leu Gln Leu Ser Phe Asp Leu Tyr
        995                 1000                1005

Asn Lys Tyr Lys Leu Lys Leu Glu Arg Leu Phe Asp Lys Lys Lys Thr
    1010                1015                1020

Val Gly Lys Tyr Lys Met Gln Ile Lys Lys Leu Thr Leu Leu Lys Glu
1025                1030                1035                1040

Gln Leu Glu Ser Lys Leu Asn Ser Leu Asn Asn Pro Lys His Val Leu
                1045                1050                1055

Gln Asn Phe Ser Val Phe Phe Asn Lys Lys Lys Glu Ala Glu Ile Ala
            1060                1065                1070

Glu Thr Glu Asn Thr Leu Glu Asn Thr Lys Ile Leu Leu Lys His Tyr
        1075                1080                1085

Lys Gly Leu Val Lys Tyr Tyr Asn Gly Glu Ser Ser Pro Leu Lys Thr
    1090                1095                1100

Leu Ser Glu Glu Ser Ile Gln Thr Glu Asp Asn Tyr Ala Ser Leu Glu
1105                1110                1115                1120

Asn Phe Lys Val Leu Ser Lys Leu Glu Gly Lys Leu Lys Asp Asn Leu
                1125                1130                1135

Asn Leu Glu Lys Lys Lys Leu Ser Tyr Leu Ser Ser Gly Leu His His
            1140                1145                1150

Leu Ile Ala Glu Leu Lys Glu Val Ile Lys Asn Lys Asn Tyr Thr Gly
        1155                1160                1165

Asn Ser Pro Ser Glu Asn Asn Thr Asp Val Asn Asn Ala Leu Glu Ser
    1170                1175                1180

Tyr Lys Lys Phe Leu Pro Glu Gly Thr Asp Val Ala Thr Val Val Ser
1185                1190                1195                1200

Glu Ser Gly Ser Asp Thr Leu Glu Gln Ser Gln Pro Lys Lys Pro Ala
                1205                1210                1215

Ser Thr His Val Gly Ala Glu Ser Asn Thr Ile Thr Thr Ser Gln Asn
            1220                1225                1230

Val Asp Asp Glu Val Asp Val Ile Ile Val Pro Ile Phe Gly Glu
        1235                1240                1245

Ser Glu Glu Asp Tyr Asp Asp Leu Gly Gln Val Val Thr Gly Glu Ala
    1250                1255                1260

Val Thr Pro Ser Val Ile Asp Asn Ile Leu Ser Lys Ile Glu Asn Glu
1265                1270                1275                1280

Tyr Glu Val Leu Tyr Leu Lys Pro Leu Ala Gly Val Tyr Arg Ser Leu
                1285                1290                1295

Lys Lys Gln Leu Glu Asn Asn Val Met Thr Phe Asn Val Asn Val Lys
            1300                1305                1310

Asp Ile Leu Asn Ser Arg Phe Asn Lys Arg Glu Asn Phe Lys Asn Val
        1315                1320                1325

Leu Glu Ser Asp Leu Ile Pro Tyr Lys Asp Leu Thr Ser Ser Asn Tyr
    1330                1335                1340

Val Val Lys Asp Pro Tyr Lys Phe Leu Asn Lys Glu Lys Arg Asp Lys
1345                1350                1355                1360

Phe Leu Ser Ser Tyr Asn Tyr Ile Lys Asp Ser Ile Asp Thr Asp Ile
                1365                1370                1375

Asn Phe Ala Asn Asp Val Leu Gly Tyr Tyr Lys Ile Leu Ser Glu Lys

-continued

```
                       1380            1385             1390
Tyr Lys Ser Asp Leu Asp Ser Ile Lys Lys Tyr Ile Asn Asp Lys Gln
        1395            1400             1405
Gly Glu Asn Glu Lys Tyr Leu Pro Phe Leu Asn Asn Ile Glu Thr Leu
    1410            1415             1420
Tyr Lys Thr Val Asn Asp Lys Ile Asp Leu Phe Val Ile His Leu Glu
1425            1430             1435             1440
Ala Lys Val Leu Asn Tyr Thr Tyr Glu Lys Ser Asn Val Glu Val Lys
            1445            1450             1455
Ile Lys Glu Leu Asn Tyr Leu Lys Thr Ile Gln Asp Lys Leu Ala Asp
        1460            1465             1470
Phe Lys Lys Asn Asn Asn Phe Val Gly Ile Ala Asp Leu Ser Thr Asp
    1475            1480             1485
Tyr Asn His Asn Asn Leu Leu Thr Lys Phe Leu Ser Thr Gly Met Val
    1490            1495             1500
Phe Glu Asn Leu Ala Lys Thr Val Leu Ser Asn Leu Leu Asp Gly Asn
1505            1510             1515             1520
Leu Gln Gly Met Leu Asn Ile Ser Gln His Gln Cys Val Lys Lys Gln
            1525            1530             1535
Cys Pro Gln Asn Ser Gly Cys Phe Arg His Leu Asp Glu Arg Glu Glu
        1540            1545             1550
Cys Lys Cys Leu Leu Asn Tyr Lys Gln Glu Gly Asp Lys Cys Val Glu
        1555            1560             1565
Asn Pro Asn Pro Thr Cys Asn Glu Asn Gly Gly Cys Asp Ala Asp
        1570            1575             1580
Ala Lys Cys Thr Glu Glu Asp Ser Gly Ser Asn Gly Lys Lys Ile Thr
1585            1590             1595             1600
Cys Glu Cys Thr Lys Pro Asp Ser Tyr Pro Leu Phe Asp Gly Ile Phe
            1605            1610             1615
Cys Ser Ser Ser Asn
        1620

<210> SEQ ID NO 6
<211> LENGTH: 4838
<212> TYPE: DNA
<213> ORGANISM: Plasmodium falciparum

<400> SEQUENCE: 6
gcggatccgt gacccacgaa tcctatcagg agctggttaa gaaactggaa gctttggaag    60
atgccgtcct taccggatac agcctgttcc agaaggagaa gatggtgctg aatgaaggga   120
cgagtggcac ggccgttaca accagcacac ccggttctaa agggtctgtg ctagcggtg    180 gctccggtgg gtctgtggcc tctgggggtt ccgtcgcctc cggcggcagc gtggcatcag    240
gtggctcagt ggcaagcggc ggttccggga acagtcgaag aaccaatcca tctgacaact    300
ctagcgattc cgacgccaag tcctacgccg acctcaagca ccgagtgaga aactatctcc    360
tcactatcaa ggagctgaag tacccacagt tgttcgacct cactaatcat atgctgacac    420
tgtgtgataa cattcatggc ttcaaatatc tgattgacgg ttacgaagag atcaatgaac    480
tcctgtacaa gttgaatttc tacttcgact tgctaagggc caaactgaat gacgtttgcg    540
ccaatgacta tttgtcaaatt ccattcaatt tgaagatcag agccaacgag ttggacgtat    600
tgaagaagtt ggtcttcgga tatcgcaagc ctctcgacaa catcaaggac aatgtgggaa    660
agatggaaga ttatattaaa aagaataaga agaccatcga gaacattaac gagctgatcg    720
```

-continued

| | |
|---|---|
| aagaatccaa aaagaccata gacaaaaata agaatgcaac caaggaggaa gaaaagaaga | 780 |
| agttgtacca ggcccagtac gacctgtcca tctataacaa acagcttgaa gaagcccata | 840 |
| acctcatcag cgtactggag aagcgcatag acaccctcaa gaagaatgaa atatcaaag | 900 |
| aactgctcga caagattaat gaaattaaga atcctccgcc agccaactct gggaacaccc | 960 |
| ctaacacgct gctggacaag aacaagaaga tagaggagca cgagaaagag atcaaagaga | 1020 |
| tcgccaaaac cattaagttc aacatagatt ctctctttac tgatcccctt gagctggagt | 1080 |
| actacttgag agagaagaat aagaatatag acatctccgc caaagtcgag acaaaggaat | 1140 |
| caaccgaacc taatgaatat cccaatggtg tgacgtaccc tctgtcttat aacgatatca | 1200 |
| acaacgctct caacgagctc aatagcttcg gtgacttgat taacccccttc gattatacga | 1260 |
| aagaaccctc taagaatatc tacacagaca atgagagaaa aagtttatc aacgaaatca | 1320 |
| aggagaagat caaaattgag aagaagaaaa ttgagagtga caagaaaagt tacgaagacc | 1380 |
| gcagcaaaag tctaaacgat atcactaaag agtatgaaaa gctgctgaac gagatctatg | 1440 |
| attccaaatt caacaataac atcgacctga ccaacttcga gaaaatgatg ggaaaacggt | 1500 |
| actcttacaa agtggagaaa ctgacacacc ataataccctt tgcatcctat gagaattcta | 1560 |
| agcataatct tgagaagctc accaaagctc ttaagtatat ggaggactat tctctgcgga | 1620 |
| acattgttgt ggagaaagaa ctaaagtatt acaagaatct cataagtaag atcgaaaacg | 1680 |
| agatcgagac gcttgttgag aacattaaga aggatgaaga acagttgttt gagaagaaga | 1740 |
| ttacaaaaga cgaaaataaa ccagatgaga agatcctgga ggtctccgat attgttaaag | 1800 |
| tccaagtgca gaaggtgctc ctcatgaaca agattgatga actcaagaag actcaactca | 1860 |
| ttctgaagaa cgtggagtta aaacataata tacatgtgcc gaatagttat aagcaggaga | 1920 |
| ataagcagga accatactac ctcatcgtac tcaagaaaga gatagacaaa ctgaaagtgt | 1980 |
| tcatgcccaa agtcgagagc ctgatcaacg aagagaagaa gaacattaaa actgaaggac | 2040 |
| agtcagataa ctccgagcct tccacagaag gagagataac cggacaggct accaccaagc | 2100 |
| ccggacaaca ggccggttca gctctcgaag gcgatagcgt gcaagctcaa gcacaagagc | 2160 |
| agaagcaggc acagcctcca gtgccagtgc ccgttccaga ggctaaagct caagtgccta | 2220 |
| caccaccagc tcctgtgaat aacaagaccg agaatgtcag caaactggac tacctttgaga | 2280 |
| agctctatga gttcctgaat acatcctaca tctgccacaa atatatcctc gtctctcaca | 2340 |
| gcactatgaa cgagaagatt cttaaacagt acaagataac caaggaagag gagagtaaac | 2400 |
| tgtcctcttg tgatccactg gacctgctgt tcaatatcca gaacaacatt cccgttatgt | 2460 |
| attctatgtt cgatagcctc aacaattctc tctctcaact gttcatggag atatatgaga | 2520 |
| aggagatggt ctgcaacctg tataaactca agacaacga caagattaag aaccttctgg | 2580 |
| aggaagctaa gaaggtctcc acctctgtta aaactctctc ttccagctcc atgcaaccac | 2640 |
| tgtctctcac acctcaagac aagcccgaag tgagcgctaa cgacgacacc tctcactcga | 2700 |
| ccaaccttaa taactcactg aaactgtttg agaacatcct gtctctcggc aagaataaga | 2760 |
| acatctacca agaacttatt ggacagaaat cgtccgagaa cttctacgag aagatactga | 2820 |
| aagacagcga cacattctat aacgagagct tcactaactt cgtgaaatct aaagccgatg | 2880 |
| atatcaactc tcttaacgat gaatctaaac gtaagaagct ggaagaggac atcaataagc | 2940 |
| tgaagaagac actgcaactg agcttcgacc tgtacaacaa gtacaaactg aaactggaga | 3000 |
| gactcttcga caagaagaag acagtcggca gtataagat gcagatcaag aagttgactc | 3060 |
| tgctcaagga gcagcttgaa agcaaactca actcactgaa caatccgaaa cacgtactgc | 3120 |

-continued

```
agaacttctc agtgttcttc aacaagaaga aggaagccga gatcgccgag acagagaaca      3180
ctctggagaa caccaagatt cttctcaaac actacaaagg cctcgtcaag tattataatg      3240
gcgagtcttc tcctctgaag actctctccg aggagagcat ccagaccgag ataactacg       3300 ccagcctcga aacttcaag gtcctgtcta agctcgaagg caagctgaag acaacctga        3360 acctggagaa gaagaagctc agctacctct ctagcggact gcatcacctg atcgccgagc      3420
tcaaggaagt cattaagaac aagaactaca ccggcaatag cccaagcgag aataatacag      3480
acgtgaataa cgcactggaa tcttacaaga gttcctgcc tgaaggaaca gatgtcgcca       3540
ctgtggtgtc tgaatctggc tccgacacac tggagcagtc tcaacctaag aagcctgcat      3600
ctactcatgt cggagccgag tccaataaca ttaccacatc tcagaacgtc gacgatgagg      3660
tcgatgacgt catcattgtg cctatcttcg gcgagagcga ggaggactac gatgacctcg      3720
gccaggtggt caccgtgag gctgtcactc cttccgtgat tgataacatt ctgtccaaaa       3780
tcgagaacga atacgaagtg ctctatctga aacctctggc aggcgtctat aggtctctca      3840
agaaacagct ggagaataac gtgatgacct caatgtcaa cgtgaaggac attctgaaca       3900
gccgctttaa taagagagaa aatttcaaga acgtcttgga gagcgacttg attccctata      3960
aagacctgac ctcctctaac tacgttgtca aggacccata caagttcctc aataaagaga      4020
agagggataa atttctgtct agttacaact atatcaagga ctccatcgac accgatatca      4080 attcgctaa tgatgtgctg ggtattaca agatcctgag cgaaaaatac aagtctgacc        4140
ttgactctat taaaaagtat atcaacgata agcaaggcga gaatgaaaaa tatctgccct      4200
tcctgaataa catcgaaacc ctgtacaaga cagtgaacga caaaatcgac ctcttcgtaa      4260
ttcacctgga ggccaaggtc ctcaactata cttacgagaa gagcaatgtg gaagttaaaa      4320
tcaaggagct gaactacctc aaaacaatcc aagacaagct ggcagatttc aagaaaaata      4380
acaatttcgt cggaattgca gacctgtcta ccgattataa ccacaacaat ctcctgacca      4440
agtttctgtc cactggcatg gtgttcgaaa acctcgccaa acagtgctg agcaatctgc       4500 tcgacggcaa cctgcagggc atgctgaaca tctcccagca ccaatgcgtg aagaaacagt      4560
gcccccagaa tagcggctgt ttcaggcatc tggacgagcg cgaagagtgc aagtgtctcc      4620
tgaactacaa acaagaagga gataagtgcg tggagaaccc aaaccctacc tgcaatgaaa      4680
acaatggcgg gtgtgacgcc gatgctaaat gcaccgagga agacagcggc tctaacggaa      4740
agaaaatcac atgcgagtgt actaagcccg actcctatcc actcttcgac gggattttt       4800 gctccagctc taatttaata ggcggccgca tcgatggc                              4838
```

<210> SEQ ID NO 7
<211> LENGTH: 1602
<212> TYPE: PRT
<213> ORGANISM: Plasmodium falciparum

<400> SEQUENCE: 7

```
Val Thr His Glu Ser Tyr Gln Glu Leu Val Lys Lys Leu Glu Ala Leu
 1               5                  10                  15

Glu Asp Ala Val Leu Thr Gly Tyr Ser Leu Phe Gln Lys Glu Lys Met
            20                  25                  30

Val Leu Asn Glu Gly Thr Ser Gly Thr Ala Val Thr Ser Thr Pro
        35                  40                  45

Gly Ser Lys Gly Ser Val Ala Ser Gly Gly Ser Gly Gly Ser Val Ala
    50                  55                  60
```

-continued

```
Ser Gly Gly Ser Val Ala Ser Gly Gly Ser Val Ala Ser Gly Gly Ser
 65                  70                  75                  80

Val Ala Ser Gly Gly Ser Gly Asn Ser Arg Arg Thr Asn Pro Ser Asp
                 85                  90                  95

Asn Ser Ser Asp Ser Asp Ala Lys Ser Tyr Ala Asp Leu Lys His Arg
            100                 105                 110

Val Arg Asn Tyr Leu Leu Thr Ile Lys Glu Leu Lys Tyr Pro Gln Leu
            115                 120                 125

Phe Asp Leu Thr Asn His Met Leu Thr Leu Cys Asp Asn Ile His Gly
130                 135                 140

Phe Lys Tyr Leu Ile Asp Gly Tyr Glu Glu Ile Asn Glu Leu Leu Tyr
145                 150                 155                 160

Lys Leu Asn Phe Tyr Phe Asp Leu Leu Arg Ala Lys Leu Asn Asp Val
                165                 170                 175

Cys Ala Asn Asp Tyr Cys Gln Ile Pro Phe Asn Leu Lys Ile Arg Ala
            180                 185                 190

Asn Glu Leu Asp Val Leu Lys Lys Leu Val Phe Gly Tyr Arg Lys Pro
            195                 200                 205

Leu Asp Asn Ile Lys Asp Asn Val Gly Lys Met Glu Asp Tyr Ile Lys
210                 215                 220

Lys Asn Lys Lys Thr Ile Glu Asn Ile Asn Glu Leu Ile Glu Glu Ser
225                 230                 235                 240

Lys Lys Thr Ile Asp Lys Asn Lys Asn Ala Thr Lys Glu Glu Glu Lys
                245                 250                 255

Lys Lys Leu Tyr Gln Ala Gln Tyr Asp Leu Ser Ile Tyr Asn Lys Gln
            260                 265                 270

Leu Glu Glu Ala His Asn Leu Ile Ser Val Leu Glu Lys Arg Ile Asp
            275                 280                 285

Thr Leu Lys Lys Asn Glu Asn Ile Lys Glu Leu Leu Asp Lys Ile Asn
290                 295                 300

Glu Ile Lys Asn Pro Pro Ala Asn Ser Gly Asn Thr Pro Asn Thr
305                 310                 315                 320

Leu Leu Asp Lys Asn Lys Lys Ile Glu Glu His Glu Lys Glu Ile Lys
                325                 330                 335

Glu Ile Ala Lys Thr Ile Lys Phe Asn Ile Asp Ser Leu Phe Thr Asp
            340                 345                 350

Pro Leu Glu Leu Glu Tyr Tyr Leu Arg Glu Lys Asn Lys Asn Ile Asp
            355                 360                 365

Ile Ser Ala Lys Val Glu Thr Lys Glu Ser Thr Glu Pro Asn Glu Tyr
370                 375                 380

Pro Asn Gly Val Thr Tyr Pro Leu Ser Tyr Asn Asp Ile Asn Asn Ala
385                 390                 395                 400

Leu Asn Glu Leu Asn Ser Phe Gly Asp Leu Ile Asn Pro Phe Asp Tyr
                405                 410                 415

Thr Lys Glu Pro Ser Lys Asn Ile Tyr Thr Asp Asn Glu Arg Lys Lys
            420                 425                 430

Phe Ile Asn Glu Ile Lys Glu Lys Ile Lys Ile Glu Lys Lys Lys Ile
            435                 440                 445

Glu Ser Asp Lys Lys Ser Tyr Glu Asp Arg Ser Lys Ser Leu Asn Asp
450                 455                 460

Ile Thr Lys Glu Tyr Glu Lys Leu Leu Asn Glu Ile Tyr Asp Ser Lys
465                 470                 475                 480

Phe Asn Asn Asn Ile Asp Leu Thr Asn Phe Glu Lys Met Met Gly Lys
```

-continued

```
                485                 490                 495
Arg Tyr Ser Tyr Lys Val Glu Lys Leu Thr His His Asn Thr Phe Ala
                500                 505                 510
Ser Tyr Glu Asn Ser Lys His Asn Leu Glu Lys Leu Thr Lys Ala Leu
                515                 520                 525
Lys Tyr Met Glu Asp Tyr Ser Leu Arg Asn Ile Val Val Glu Lys Glu
                530                 535                 540
Leu Lys Tyr Tyr Lys Asn Leu Ile Ser Lys Ile Glu Asn Glu Ile Glu
545                 550                 555                 560
Thr Leu Val Glu Asn Ile Lys Lys Asp Glu Glu Gln Leu Phe Glu Lys
                565                 570                 575
Lys Ile Thr Lys Asp Glu Asn Lys Pro Asp Glu Lys Ile Leu Glu Val
                580                 585                 590
Ser Asp Ile Val Lys Val Gln Val Gln Lys Val Leu Leu Met Asn Lys
                595                 600                 605
Ile Asp Glu Leu Lys Lys Thr Gln Leu Ile Leu Lys Asn Val Glu Leu
                610                 615                 620
Lys His Asn Ile His Val Pro Asn Ser Tyr Lys Gln Glu Asn Lys Gln
625                 630                 635                 640
Glu Pro Tyr Tyr Leu Ile Val Leu Lys Lys Glu Ile Asp Lys Leu Lys
                645                 650                 655
Val Phe Met Pro Lys Val Glu Ser Leu Ile Asn Glu Glu Lys Lys Asn
                660                 665                 670
Ile Lys Thr Glu Gly Gln Ser Asp Asn Ser Glu Pro Ser Thr Glu Gly
                675                 680                 685
Glu Ile Thr Gly Gln Ala Thr Thr Lys Pro Gly Gln Gln Ala Gly Ser
                690                 695                 700
Ala Leu Glu Gly Asp Ser Val Gln Ala Gln Ala Gln Glu Gln Lys Gln
705                 710                 715                 720
Ala Gln Pro Pro Val Pro Val Pro Glu Ala Lys Ala Gln Val
                725                 730                 735
Pro Thr Pro Pro Ala Pro Val Asn Asn Lys Thr Glu Asn Val Ser Lys
                740                 745                 750
Leu Asp Tyr Leu Glu Lys Leu Tyr Glu Phe Leu Asn Thr Ser Tyr Ile
                755                 760                 765
Cys His Lys Tyr Ile Leu Val Ser His Ser Thr Met Asn Glu Lys Ile
                770                 775                 780
Leu Lys Gln Tyr Lys Ile Thr Lys Glu Glu Ser Lys Leu Ser Ser
785                 790                 795                 800
Cys Asp Pro Leu Asp Leu Leu Phe Asn Ile Gln Asn Asn Ile Pro Val
                805                 810                 815
Met Tyr Ser Met Phe Asp Ser Leu Asn Asn Ser Leu Ser Gln Leu Phe
                820                 825                 830
Met Glu Ile Tyr Glu Lys Glu Met Val Cys Asn Leu Tyr Lys Leu Lys
                835                 840                 845
Asp Asn Asp Lys Ile Lys Asn Leu Leu Glu Glu Ala Lys Lys Val Ser
850                 855                 860
Thr Ser Val Lys Thr Leu Ser Ser Ser Met Gln Pro Leu Ser Leu
865                 870                 875                 880
Thr Pro Gln Asp Lys Pro Glu Val Ser Ala Asn Asp Asp Thr Ser His
                885                 890                 895
Ser Thr Asn Leu Asn Asn Ser Leu Lys Leu Phe Glu Asn Ile Leu Ser
                900                 905                 910
```

-continued

Leu Gly Lys Asn Lys Asn Ile Tyr Gln Glu Leu Ile Gly Gln Lys Ser
            915                 920                 925

Ser Glu Asn Phe Tyr Glu Lys Ile Leu Lys Asp Ser Asp Thr Phe Tyr
        930                 935                 940

Asn Glu Ser Phe Thr Asn Phe Val Lys Ser Lys Ala Asp Asp Ile Asn
945                 950                 955                 960

Ser Leu Asn Asp Glu Ser Lys Arg Lys Leu Glu Glu Asp Ile Asn
            965                 970                 975

Lys Leu Lys Lys Thr Leu Gln Leu Ser Phe Asp Leu Tyr Asn Lys Tyr
            980                 985                 990

Lys Leu Lys Leu Glu Arg Leu Phe Asp Lys Lys Thr Val Gly Lys
            995                1000                1005

Tyr Lys Met Gln Ile Lys Lys Leu Thr Leu Leu Lys Glu Gln Leu Glu
           1010                1015                1020

Ser Lys Leu Asn Ser Leu Asn Asn Pro Lys His Val Leu Gln Asn Phe
1025                1030                1035                1040

Ser Val Phe Phe Asn Lys Lys Lys Glu Ala Glu Ile Ala Glu Thr Glu
                   1045                1050                1055

Asn Thr Leu Glu Asn Thr Lys Ile Leu Leu Lys His Tyr Lys Gly Leu
           1060                1065                1070

Val Lys Tyr Tyr Asn Gly Glu Ser Ser Pro Leu Lys Thr Leu Ser Glu
           1075                1080                1085

Glu Ser Ile Gln Thr Glu Asp Asn Tyr Ala Ser Leu Glu Asn Phe Lys
           1090                1095                1100

Val Leu Ser Lys Leu Glu Gly Lys Leu Lys Asp Asn Leu Asn Leu Glu
1105                1110                1115                1120

Lys Lys Lys Leu Ser Tyr Leu Ser Ser Gly Leu His His Leu Ile Ala
                   1125                1130                1135

Glu Leu Lys Glu Val Ile Lys Asn Lys Asn Tyr Thr Gly Asn Ser Pro
           1140                1145                1150

Ser Glu Asn Asn Thr Asp Val Asn Asn Ala Leu Glu Ser Tyr Lys Lys
           1155                1160                1165

Phe Leu Pro Glu Gly Thr Asp Val Ala Thr Val Ser Glu Ser Gly
           1170                1175                1180

Ser Asp Thr Leu Glu Gln Ser Gln Pro Lys Lys Pro Ala Ser Thr His
1185                1190                1195                1200

Val Gly Ala Glu Ser Asn Thr Ile Thr Thr Ser Gln Asn Val Asp Asp
           1205                1210                1215

Glu Val Asp Asp Val Ile Ile Val Pro Ile Phe Gly Glu Ser Glu Glu
           1220                1225                1230

Asp Tyr Asp Asp Leu Gly Gln Val Val Thr Gly Glu Ala Val Thr Pro
           1235                1240                1245

Ser Val Ile Asp Asn Ile Leu Ser Lys Ile Glu Asn Glu Tyr Glu Val
           1250                1255                1260

Leu Tyr Leu Lys Pro Leu Ala Gly Val Tyr Arg Ser Leu Lys Lys Gln
1265                1270                1275                1280

Leu Glu Asn Asn Val Met Thr Phe Asn Val Asn Val Lys Asp Ile Leu
                   1285                1290                1295

Asn Ser Arg Phe Asn Lys Arg Glu Asn Phe Lys Asn Val Leu Glu Ser
                   1300                1305                1310

Asp Leu Ile Pro Tyr Lys Asp Leu Thr Ser Ser Asn Tyr Val Val Lys
           1315                1320                1325

-continued

```
Asp Pro Tyr Lys Phe Leu Asn Lys Glu Lys Arg Asp Lys Phe Leu Ser
    1330                1335                1340
Ser Tyr Asn Tyr Ile Lys Asp Ser Ile Asp Thr Asp Ile Asn Phe Ala
1345                1350                1355                1360
Asn Asp Val Leu Gly Tyr Tyr Lys Ile Leu Ser Glu Lys Tyr Lys Ser
                1365                1370                1375
Asp Leu Asp Ser Ile Lys Lys Tyr Ile Asn Asp Lys Gln Gly Glu Asn
                1380                1385                1390
Glu Lys Tyr Leu Pro Phe Leu Asn Asn Ile Glu Thr Leu Tyr Lys Thr
            1395                1400                1405
Val Asn Asp Lys Ile Asp Leu Phe Val Ile His Leu Glu Ala Lys Val
        1410                1415                1420
Leu Asn Tyr Thr Tyr Glu Lys Ser Asn Val Glu Val Lys Ile Lys Glu
1425                1430                1435                1440
Leu Asn Tyr Leu Lys Thr Ile Gln Asp Lys Leu Ala Asp Phe Lys Lys
                1445                1450                1455
Asn Asn Asn Phe Val Gly Ile Ala Asp Leu Ser Thr Asp Tyr Asn His
                1460                1465                1470
Asn Asn Leu Leu Thr Lys Phe Leu Ser Thr Gly Met Val Phe Glu Asn
            1475                1480                1485
Leu Ala Lys Thr Val Leu Ser Asn Leu Leu Asp Gly Asn Leu Gln Gly
        1490                1495                1500
Met Leu Asn Ile Ser Gln His Gln Cys Val Lys Lys Gln Cys Pro Gln
1505                1510                1515                1520
Asn Ser Gly Cys Phe Arg His Leu Asp Glu Arg Glu Glu Cys Lys Cys
                1525                1530                1535
Leu Leu Asn Tyr Lys Gln Glu Gly Asp Lys Cys Val Glu Asn Pro Asn
                1540                1545                1550
Pro Thr Cys Asn Glu Asn Asn Gly Gly Cys Asp Ala Asp Ala Lys Cys
            1555                1560                1565
Thr Glu Glu Asp Ser Gly Ser Asn Gly Lys Lys Ile Thr Cys Glu Cys
        1570                1575                1580
Thr Lys Pro Asp Ser Tyr Pro Leu Phe Asp Gly Ile Phe Cys Ser Ser
1585                1590                1595                1600
Ser Asn

<210> SEQ ID NO 8
<211> LENGTH: 12
<212> TYPE: PRT
<213> ORGANISM: Artificial Sequence
<220> FEATURE:
<223> OTHER INFORMATION: synthetic peptide

<400> SEQUENCE: 8

Met Arg Gly Ser His His His His His His Gly Ser
1               5                   10
```